(12) United States Patent
Xiao et al.

(10) Patent No.: US 9,233,990 B2
(45) Date of Patent: Jan. 12, 2016

(54) ORGANOAMINOSILANES AND METHODS FOR MAKING SAME

(71) Applicant: AIR PRODUCTS AND CHEMICALS, INC., Allentown, PA (US)

(72) Inventors: Manchao Xiao, San Diego, CA (US); Matthew R. MacDonald, Laguna Niguel, CA (US); Richard Ho, Anaheim, CA (US); Xinjian Lei, Vista, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 14/625,158

(22) Filed: Feb. 18, 2015

(65) Prior Publication Data
US 2015/0246937 A1 Sep. 3, 2015

Related U.S. Application Data

(60) Provisional application No. 61/946,164, filed on Feb. 28, 2014.

(51) Int. Cl.
*C07F 7/10* (2006.01)
*C07F 7/02* (2006.01)

(52) U.S. Cl.
CPC .. *C07F 7/10* (2013.01); *C07F 7/025* (2013.01)

(58) Field of Classification Search
CPC .................................. C07F 7/10; C07F 7/0812
USPC .................................................. 556/406, 410
See application file for complete search history.

(56) References Cited

U.S. PATENT DOCUMENTS

| 4,965,367 | A | * | 10/1990 | Baney et al. .......... C07F 7/0801 548/110 |
| 6,072,085 | A | | 6/2000 | Verdaguer et al. |
| 6,963,003 | B2 | | 11/2005 | Qin |
| 7,875,556 | B2 | | 1/2011 | Xiao et al. |
| 2006/0258173 | A1 | | 11/2006 | Xiao et al. |
| 2011/0262642 | A1 | | 10/2011 | Xiao et al. |
| 2012/0277457 | A1 | | 11/2012 | Lehmann et al. |

FOREIGN PATENT DOCUMENTS

| JP | 49110632 | 3/1973 |
| KR | 101040325 | 6/2011 |

OTHER PUBLICATIONS

L. Hao, et al, "Homogeneous Catalytic Hydrosilylation of Pyridines", Agnew. Chem. Int. Ed., 1998, 3126-3129.
H. Hashimoto, et al, "Stoichiometric Hydrosilylation of Nitriles and Catalytic Hydrosilylation of Imines and Ketones Using a u-Silane Diruthenium Complex", Organometallics, 2003, 2199-2201.
H. Gruber-Woelfler, et al, "Titanocene-Catalyzed Hydrosilylation of Imines: Experimental and Computational Investigations of the Catalytically Active Species", Organometallics, 2009, 2546-2553.
C. Cheng, et al, "Iridium-Catalyzed Reduction of Secondary Amides to Secondary Amines and Imines by Diethylsilane", J. Am. Chem. Soc., 2012, 11304-11307.
I. Ojima, et al, "A Novel Method for the Reduction of Schiff Bases Using Catalytic Hydrosilylation", Tetrahedron Letters, 1973, 2475-2478.
I. Iovel, et al, "Hydrosilylation of Heterocyclic Aldimines Catalyzed by Transition Metal Complexes", Chemistry of Heterocyclic Compounds, 2002, 46-53.
L. D. Field, et al, "Iridium(I)-Catalysed Tandem Hydrosilylation-Protodesilylation of Imines", European Journal of Organic Chemistry, 2005, 2881-2883.
L. C. Misal Castro, et al, "NHC-carbene cyclopentadienyl iron based catalyst for a general and efficient hydrosilylation of imines", Chemical Communications, 2012, 151-153.
T. A. Sladkova, et al, "The effect of structure of silicon-containing nitrile on orientation of its catalytic reduction", 1965.
K. A. Andrianov, et al, "Reaction of the amino group of organoaminosilanes and organosilazanes with electron-donating solvents", 1973.
A. M. Krapivin, et al, "The NMR study and CNDO/2 molecular orbital calculation of silacyclobutanes", 1980.

* cited by examiner

*Primary Examiner* — Porfirio Nazario Gonzalez
*Assistant Examiner* — Kofi Adzamli
(74) *Attorney, Agent, or Firm* — Rosaleen P. Morris-Oskanian

(57) ABSTRACT

Organoaminosilanes, such as without limitation di-iso-propylaminosilane (DIPAS), are precursors for the deposition of silicon containing films such as silicon-oxide and silicon-nitride films. Described herein are methods to make organoaminosilane compounds, or other compounds such as organoaminodisilanes and organoaminocarbosilanes, via the catalytic hydrosilylation of an imine by a silicon source comprising a hydridosilane.

1 Claim, No Drawings

ORGANOAMINOSILANES AND METHODS FOR MAKING SAME

CROSS REFERENCE TO RELATED APPLICATIONS

This application claims the priority benefit of U.S. Provisional Application Ser. No. 61/946,164 filed Feb. 28, 2014 which is incorporated herein by reference in its entirety.

BACKGROUND OF THE INVENTION

Described herein are methods for making organoaminosilane compounds that may be useful, for example, as chemical precursor for depositing a silicon-containing film. Also described herein are compounds, more specifically organoamines, organoaminosilane, organoaminodisilane, and/or organoaminocarbosilane compounds, that are suitable for use in a variety of industrial applications.

Organoaminosilanes containing the —$SiH_3$ or —$SiH_2$— moieties are desirable precursors for the deposition of silicon-containing films such as, without limitation, silicon oxide and silicon nitride films or doped versions thereof. For example, volatile compounds such as without limitation organoaminosilanes, organoaminodisilanes, and/or organoaminocarbosilanes are important precursors used for the deposition of silicon-containing films in the manufacture of semiconductor devices. One particular embodiment of an organoaminosilane compound is di-iso-propylaminosilane (DIPAS), which has previously been shown to exhibit desirable physical properties for the controlled deposition of such films. Although DIPAS can be prepared by the direct reaction of di-iso-propylamine (DIPA) or lithium-di-iso-propylamide with monochlorosilane (MCS) or monochlorodisilane (MCDS), MCS or MCDS is not an abundant commodity chemical and is therefore subject to limited availability and price instability. Furthermore, synthesis of organoaminosilanes using MCS may produce stoichiometric amounts of amine hydrochloride salts that can be highly absorbent thereby complicating recovery of organoaminosilane products.

The prior art describes some methods for the production of organoaminosilane compounds. Japanese Patent JP49-1106732 describes a method for preparing silylamines by the reaction of an imine and a hydridosilane in the presence of a rhodium (Rh) complex. Exemplary silylamines that were prepared include: $PhCH_2N(Me)SiEt_3$, $PhCH_2N(Me)SiHPh_2$, $PhCH_2N(Ph)SiEt_3$, and $PhMeCHN(Ph)SiHEt_2$ wherein "Ph" means phenyl, "Me" means methyl, and "Et" means ethyl.

U.S. Pat. No. 6,072,085 describes a method for preparing a secondary amine from a reaction mixture comprising an imine, a nucleophilic activator, a silane, and a metal catalyst. The catalyst acts to catalyze the reduction of the imine by a hydrosilylation reaction.

U.S. Pat. No. 6,963,003, which is owned by the assignee of the present application, provides a method for preparing an organoaminosilane compound comprising reacting a stoichiometric excess of at least one amine selected from the group consisting of secondary amines having the formula $R^1R^2NH$, primary amines having the formula $R^2NH_2$ or combinations thereof with at least one chlorosilane having the formula $R^3{}_nSiCl_{4-n}$, under anhydrous conditions sufficient such that a liquid comprising the aminosilane product and an amine hydrochloride salt is produced wherein $R^1$ and $R^2$ can each independently be a linear, cyclic or branched alkyl group having 1 to 20 carbon atoms; $R^3$ can be a hydrogen atom, an amine group, or a linear, cyclic or branched alkyl group having 1 to 20 carbon atoms; and n is a number ranging from 1 to 3.

U.S. Pat. No. 7,875,556, which is owned by the assignee of the present application, describes a method for making an organoaminosilane by reacting an acid with an arylsilane in the presence of a solvent, adding a secondary amine and tertiary amine, and removing the reaction byproduct using phase separation and the solvent using distillation.

U.S. Publ. No. 2012/0277457, which is owned by the assignee of the present application, describes a method for making an organoaminosilane compound having the following formula:

$$H_3SiNR^1R^2$$

wherein $R^1$ and $R^2$ are each independently selected from $C_1$-$C_{10}$ linear, branched or cyclic, saturated or unsaturated, aromatic, heterocyclic, substituted or unsubstituted alkyl groups wherein $R^1$ and $R^2$ are linked to form a cyclic group or wherein $R^1$ and $R^2$ are not linked to form a cyclic group comprising the steps of: reacting a halosilane having the formula $H_nSiX_{4-n}$ wherein n is 0, 1, or 2 and X is Cl, Br, or a mixture of Cl and Br, with an amine to provide a slurry comprising a haloaminosilane compound $X_{4-n}H_{n-1}SiNR^1R^2$ wherein n is a number selected from 1, 2 and 3; and X is a halogen selected from Cl, Br, or a mixture of Cl and Br; and introducing into the slurry a reducing agent wherein at least a portion of the reducing agent reacts with the haloaminosilane compound and provides an end product mixture comprising the aminosilane compound.

Korean Patent No. 10-1040325 provides a method for preparing an alkylaminosilane which involves reacting a secondary amine and trichloroalkylsilane in an anhydrous atmosphere and in the presence of a solvent to form an alkyl aminochlorosilane intermediate and a metal hydride $LiAlH_4$ is added to the alkyl aminochlorosilane intermediate as a reducing agent to form the alkylaminosilane. The alkylaminosilane is then subjected to a distillation process to separate and purify the alkylaminosilane.

Reference article entitled "Homogeneous Catalytic Hydrosilylation of Pyridines", L. Hao et al., Angew. Chem., Int. Ed., Vol. 37, 1998, pp. 3126-29 describes the hydrosilylation of pyridines, e.g. $RC_5H_4N$ (R=H, 3-Me, 4-Me, 3-$CO_2Et$), by $PhSiH_2Me$, $Ph_2SiH_2$ and $PhSiH_3$ in the presence of a titanocene complex catalyst such as a [$Cp_2TiMe_2$], which provided high yields of 1-silylated tetrahydropyridine derivatives and the intermediate silyltitanocene adduct, $Cp_2Ti(SiHMePh)(C_5H_5N)$ (I).

Reference article entitled "Stoichiometric Hydrosilylation of Nitriles and Catalytic Hydrosilylation of Imines and Ketones Using a μ-Silane Diruthenium Complex", H. Hashimoto et al., Organometallics, Vol. 22, 2003, pp. 2199-2201 describes a method to synthesize μ-iminosilyl complexes $Ru_2(CO)_4(\mu\text{-dppm})(\mu\text{-SiTol}_2)(\mu\text{-RCH:NSiTol}_2)$ (R=Me, Ph, t-Bu, $CH:CH_2$) in high yields during the stoichiometric reactions of a diruthenium complex having Ru—H—Si interactions, $\{Ru(CO)_2(SiTol_2H)\}_2(\mu\text{-dppm})(\mu\text{-}\eta^2{:}\eta^2\text{-}H_2SiTol_2)$, with nitriles RCN.

Reference article entitled "Titanocene-Catalyzed Hydrosilylation of Imines: Experimental and Computational Investigations of the Catalytically Active Species", H. Gruber-Woelfler et al., Organometallics, Vol. 28, 2009, pp. 2546-2553 described the asymmetrical catalytic hydrosilylation of imines using (R,R)-ethylene-1,2-bis($\eta^5$-4,5,6,7-tetrahydro-1-indenyl)titanium (R)-1,1'-binaphth-2-olate (1) and (S,S)-ethylene-1,2-bis($\eta^5$-4,5,6,7-tetrahydro-1-indenyl)titanium dichloride (2) as catalyst precursors. After activation with RLi (R=alkyl, aryl) and a silane, these complexes are known catalysts for hydrosilylation reactions.

Reference article "Iridium-Catalyzed Reduction of Secondary Amides to Secondary Amines and Imines by Diethylsilane", C. Cheng et al., J. Am. Chem. Soc., Vol. 134, 2012, pp. 110304-7, describes the catalytic reduction of secondary amides to imines and secondary amines by using iridium catalysts such as $[Ir(COE)_2Cl]_2$ with diethylsilane as reductant.

The prior art synthesis reactions described above suffer from various deficiencies. For example, in the synthesis routes that do not use a catalyst, the synthesis of organoaminosilane require multiple steps using, for example, (a) arylsilane, triflic acid, secondary amine, and tertiary amine, (b) silylhalogen, excess secondary amine, and metal hydride, or (c) silylhalogen, alkali metal amide, and metal hydride. Each of these synthesis routes requires significant cooling to manage highly exothermic reactions and produce significant amounts of salt byproducts that must be subsequently removed by filtration process.

Alternatively, the synthesis reactions described above that do involve catalytic hydrosilylation of imines, are generally used for the synthesis of secondary amines or, alternatively, for highlighting fundamentally unique catalysts. As such, the aforementioned references do not describe a method for the synthesis, isolation, and purification of organoaminosilanes to be used, for example, as precursors for the deposition of silicon-containing films. It should be noted further that there are no description in the above references wherein, silicon-containing sources such as silane ($SiH_4$), disilane ($Si_2H_6$), or methylsilane ($MeSiH_3$) gas are used as the Si—H starting material or silicon source material for the catalytic hydrosilylation of imines to form organoaminosilane or organoaminodisilane compounds, such as, for example, di-iso-propylaminosilane (DIPAS), di-iso-propylaminodisilane (DIPADS), and di-iso-propylaminomethylsilane. Furthermore, there is no prior art that teaches the use of complexes of alkaline earth metals such as Ca, Sr, Ba, which are more abundant and less expensive than many transition metals, as catalysts for the hydrosilylation of imines, whether it be for the synthesis of organoaminosilanes, organoaminodisilanes, and organoaminocarbosilanes or the synthesis of organoamines.

Accordingly there is a need to provide a method of making compounds such as, without limitation, organoamines, organoaminosilanes (e.g., DIPAS), organoaminodisilanes (e.g., DIPADS), and organoaminocarbosilanes, using commercially available reagents in relatively high yields via the catalytic hydrosilylation of imines. There is also a need to provide a method of making organoaminosilanes, such as without limitation, DIPAS, by a means that eliminates or facilitates the separation of the product from reaction mixture. There is a need to provide methods of making organoaminosilanes and/or organoamines that reduces the overall production costs by reducing the costs of reagents used and/or reducing agents. There is a need to provide a method of making organoaminosilanes and/or organoamines that eliminates hazards associated with highly exothermic reactions such as those involving triflic acid, metal amide, and metal hydride reagents. There is a need to provide a method of making organoaminosilanes and/or organoamines that avoids using halosilane starting materials, such that there are reduced halide impurities in the purified product in order to avoid potential halides contamination if the compound is used as a precursor for depositing silicon-containing films. There is also a need for synthesis of compounds such as, without limitation, organoamines, organoaminosilanes, organoaminodisilanes, or organoaminocarbosilanes via hydrosilylation of imines using cheaper, more earth abundant metal catalysts compared to the currently widely used precious metal (Ru, Rh, Ir, Pd, and Pt) catalysts.

BRIEF SUMMARY OF THE INVENTION

Described herein is a method for making compounds, more specifically organoaminosilanes, organoaminodisilanes, organoaminocarbosilanes and/or organoamines, which provides one or more of the following advantages over prior art methods to make such compounds: (a) avoids the use of chlorosilane reagents which could lead to chlorine impurities in the end product thereby eliminating chloride contamination when the end product is being used as precursors to deposit a silicon containing film; (b) avoids the need for additional filtration steps to remove amine-hydrochloride or alkali metal salt byproducts which are common in prior art methods, and/or (c) avoids the use of pyrophoric alkyllithium, metal hydride reagents, or extremely corrosive reagents such as triflic acid. In this regard, the methods described herein improve upon the prior art methods for making compounds such as organoaminosilanes, organoaminodisilanes, organoaminocarbosilanes, and organoamines in one or more of the following ways: provides increased product purity, improves the yield of end product, and/or avoids potential environmental health and safety issues. The term "organoaminosilane" as used herein means a compound that includes at least one N atom, at least one carbon-containing group, and at least one Si atom and includes, without limitation, organoaminosilanes, organoaminodisilanes, and organoaminocarbosilanes.

In one aspect, described herein is a method for preparing a compound selected from the group consisting of an organoaminosilane, an organoaminodisilane, and an organoaminocarbosilane comprising the steps of: reacting an imine having a formula R—N=CR'R" wherein R, R' and R" are each independently selected from hydrogen, a $C_{1-10}$ linear alkyl group, a $C_{3-10}$ branched alkyl group, a $C_{3-10}$ cyclic alkyl group, a $C_{2-10}$ alkenyl group, a $C_{4-10}$ aromatic group, a $C_{4-10}$ heterocyclic group, a $C_{1-10}$ linear organoamino group, a $C_{2-10}$ branched organoamino group, a silyl group, a $C_{1-10}$ linear carbosilyl group, and a $C_{2-10}$ branched carbosilyl group and wherein at least one of R' and R" or R and R' or none of R' and R" or R and R' are be linked to form a substituted or an unsubstituted cyclic ring and a silicon source comprising a hydridosilane in the presence of a catalyst under conditions sufficient for the silicon source and imine to react and provide the compound. In certain embodiments of the imine having formula R—N=CR'R", at least one of R' and R", R and R', or both R' and R" and R and R' in the formula are linked to form the substituted or unsubstituted cyclic ring. In alternative embodiments of the imine having formula R—N=CR'R", neither R' and R" nor R and R' in the formula are linked to form the substituted or unsubstituted cyclic ring. In one particular embodiment of the method described herein, the reacting step is conducted in the presence of a solvent. In an alternative embodiment of the method described herein, the reacting step is conducted in the absence of a solvent.

In another aspect, there is provided a method for preparing an organoamine having a formula HN(R)(CHR'R") wherein R, R' and R" are each independently selected from hydrogen, a $C_{1-10}$ linear alkyl group, a $C_{3-10}$ branched alkyl group, a $C_{3-10}$ cyclic alkyl group, a $C_{2-10}$ alkenyl group, a $C_{4-10}$ aromatic group, a $C_{4-10}$ heterocyclic group, a $C_{1-10}$ linear organoamino group, a $C_{2-10}$ branched organoamino group, a $C_{1-10}$ linear carbosilyl group, and a $C_{2-10}$ branched carbosilyl group wherein at least one of R' and R" or R and R', or none of R' and R" or R and R' are linked to form a substituted or an unsubstituted cyclic ring comprising the steps of: forming a compound selected from an organoaminosilane, an organoaminodisilane, and an organoaminocarbosilane by reacting an imine having a formula R—N═CR'R" wherein R, R' and R" are each independently selected from hydrogen, a $C_{1-10}$ linear alkyl group, a $C_{3-10}$ branched alkyl or $C_{3-10}$ cyclic alkyl, $C_{2-10}$ alkenyl, $C_{4-10}$ aromatic, $C_{4-10}$ heterocyclic, $C_{1-10}$ linear or $C_{2-10}$ branched organoamino groups, a silyl group, or $C_{1-10}$ linear carbosilyl or $C_{2-10}$ branched carbosilyl groups wherein at least one of R' and R", R and R', or none of R' and R" and R and R' are linked to form a substituted or unsubstituted cyclic ring and a silicon source comprising a hydridosilane in the presence of an alkaline earth metal catalyst under reaction conditions sufficient for the imine and silicon source to react and provide the compound; reacting the compound with a proton source under conditions sufficient to provide the organoamine. In certain embodiments, the proton source is selected from the group consisting of water, alcohol, or Brønsted acid.

In a further aspect, there is provided organoaminocarbosilane compound represented by the following structures:

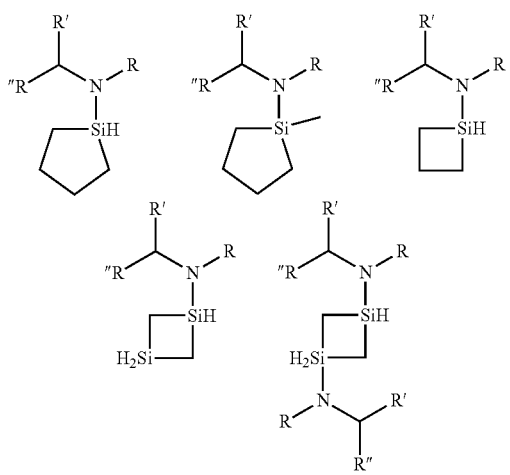

wherein R, R' and R" are each independently selected from hydrogen, a $C_{1-10}$ linear alkyl group, a $C_{3-10}$ branched alkyl group, a $C_{3-10}$ cyclic alkyl group, a $C_{2-10}$ alkenyl group, a $C_{4-10}$ aromatic group, a $C_{4-10}$ heterocyclic group, a $C_{1-10}$ linear organoamino group, a $C_{2-10}$ branched organoamino groups, a silyl group, a $C_{1-10}$ linear carbosilyl group, or a $C_{2-10}$ branched carbosilyl groups and wherein at least one of R' and R", or R and R', or none of R' and R" or R and R' are be linked to form a substituted or unsubstituted cyclic ring.

DETAILED DESCRIPTION OF THE INVENTION

Methods for preparing compounds such as organoaminosilanes, organoaminodisilanes, organoaminocarbosilanes, and organoamines are described herein using an imine having a formula R—N═CR'R" wherein R, R' and R" are each independently selected from hydrogen, a $C_{1-10}$ linear alkyl group, a $C_{3-10}$ branched alkyl group, a $C_{3-10}$ cyclic alkyl group, a $C_{2-10}$ alkenyl group, a $C_{4-10}$ aromatic group, a $C_{4-10}$ heterocyclic group, a $C_{1-10}$ linear organoamino group, a $C_{2-10}$ branched organoamino group, a silyl group, a $C_{1-10}$ linear carbosilyl group, and a $C_{2-10}$ branched carbosilyl group and wherein R' and R" or R and R' can be linked to form a substituted or an unsubstituted cyclic ring. In certain embodiments of the imine having formula R—N═CR'R", R' and R" or R and R' in the formula are linked to form the substituted or unsubstituted cyclic ring. In these embodiments, the imine can be synthesized by condensing a primary amine having the formula $RNH_2$, with a ketone or aldehyde having the formula R'R"C═O. In alternative embodiments of the imine having formula R—N═CR'R", R' and R" or R and R' in the formula are not linked to form the substituted or unsubstituted cyclic ring.

In the formulas above and throughout the description, the term "alkyl" denotes a linear or branched functional group having from 1 to 10 or from 3 to 10 carbon atoms, respectively. Exemplary linear alkyl groups include, but are not limited to, methyl, ethyl, n-propyl, n-butyl, n-pentyl, and hexyl. Exemplary branched alkyl groups include, but are not limited to, isopropyl, isobutyl, sec-butyl, tert-butyl, iso-pentyl, tert-pentyl, isohexyl, and neohexyl. In certain embodiments, the alkyl group may have one or more functional groups such as, but not limited to, an alkoxy group, a dialkylamino group, an carbosilyl group, or combinations thereof, attached thereto. In other embodiments, the alkyl group does not have one or more functional groups attached thereto.

In the formulas above and throughout the description, the term "cyclic alkyl" denotes a cyclic functional group having from 3 to 10 or from 4 to 10 carbon atoms. Exemplary cyclic alkyl groups include, but are not limited to, cyclobutyl, cyclopentyl, cyclohexyl, and cyclooctyl groups.

In the formulas above and throughout the description, the term "aryl" denotes an aromatic cyclic functional group having from 5 to 10 carbon atoms. Exemplary aryl groups include, but are not limited to, phenyl, benzyl, chlorobenzyl, tolyl, and o-xylyl. In some embodiments, the aromatic cyclic group can have other elements such as oxygen, or nitrogen. Exemplary such groups include, but not limited to, pyrollyl, furanyl, pyridinyl, pyridazinyl.

In the formulas above and throughout the description, the term "alkenyl group" denotes a group which has one or more carbon-carbon double bonds and has from 2 to 10 or from 2 to 6 carbon atoms. Exemplary alkenyl groups include, but are not limited to, vinyl or allyl groups.

In the formulas above and throughout the description, the term "alkynyl group" denotes a group which has one or more carbon-carbon triple bonds and has from 2 to 10 or from 2 to 6 carbon atoms.

In the formulas above and throughout the description, the term "carbosilane" denotes an organosilane comprising carbon, hydrogen, and silicon having from 1 to 10 carbon atoms and from 1 to 10 silicon atoms, and which contains at least one Si—C bond. Examples of carbosilanes include, without limitation, methylsilane, ethylsilane, diethylsilane, dimethylsilane, triethylsilane, 1,2-dimethyldisilane,1,4-disilabutane, 2-methyl-1,3-disilapropane, 1,3-disilapropane, 1-silacyclopentane, 1-methyl-1-silacyclopentane, 1-silacyclobutane, 1,3-disilacyclobutane, and phenylsilane.

In the formulas above and throughout the description, the term "carbosilyl" denotes an organosilyl group comprising carbon, hydrogen, and silicon having from 1 to 10 carbon atoms and from 1 to 10 silicon atoms, and which contains at least one Si—C bond. Examples of carbosilyl groups include, without limitation, methylsilyl (—$SiMeH_2$), ethylsilyl (—$SiEtH_2$), diethylsilyl (—$SiEt_2H$), dimethylsilyl (—$SiMe_2H$), triethylsilyl (—$SiEt_3$), trimethylsilyl (—$SiMe_3$), 1,2-dimethyldisilyl (—$SiMeHSiMeH_2$),1,4-disilabutyl (—$SiH_2CH_2CH_2SiH_3$), dimethylvinylsilyl (—$SiMe_2CH═CH_2$), and phenylsilyl (—$SiPhH_2$).

In the formulas above and throughout the description, the term "silyl" denotes the unsubstituted silyl group (—SiH$_3$).

In formulas above and throughout the description, the term "organoamino" denotes a dialkylamino, alkylamino, or arylalkylamino group which may have from 1 to 10, or from 1 to 4 carbon atoms. Exemplary organoamino groups include, but are not limited to, dimethylamino (Me$_2$N—), diethylamino (Et$_2$N—), di-iso-propylamino ($^i$Pr$_2$N—), iso-propyl-sec-butylamino, N-sec-butyl-N-iso-propylamino, 1-(N-ethyl-N-cyclohexylamino, N-phenyl-N-iso-propylamino, tert-butylamino ($^t$BuNH—), tert-pentylamino ($^t$AmNH—), n-propylamino ($^n$PrNH—), and iso-propylamino ($^i$PrNH—).

In certain embodiments of the formulas described herein, a substituent such as a cyclic ring may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In alternative embodiments, the substitutent is not unsubstituted.

The method described herein involves the catalytic hydrosilylation of imines as an alternative route to the synthesis of compounds such as organoaminosilane, organoaminodisilane, and organoaminocarbosilane which can be used, without limitation, as precursors in the deposition of silicon-containing films. For example, in one embodiment, the organoaminosilane $^i$Pr$_2$N—SiH$_3$ could be conveniently synthesized by reacting the imine N-iso-propyl-iso-propylidenimine with a silicon source of silane gas SiH$_4$. In another embodiment, the organoaminodisilane $^i$Pr$_2$N—SiH$_2$SiH$_3$ could be obtained in a similar fashion by reacting the imine N-iso-propyl-iso-propylidenimine with a silicon source of disilane gas Si$_2$H$_6$. The method described herein can be used, for example, to prepare other organoaminosilane, organoaminodisilane, or organoaminocarbosilane compounds such as, without limitation, (organoamino)SiH$_3$, (organoamino)SiH$_2$SiH$_3$, (organoamino)SiH$_2$SiH$_2$(organoamino), (organoamino)SiH$_2$CH$_2$CH$_2$SiH$_3$, (organoamino)SiH$_2$CH$_2$CH$_2$SiH$_2$(organoamino), (organoamino)SiHEt$_2$, (organoamino)SiH(CH$_2$CH$_2$CH$_2$CH$_2$), (organoamino)SiMe(CH$_2$CH$_2$CH$_2$CH$_2$), (organoamino)SiH(CH$_2$CH$_2$CH$_2$), (organoamino)SiH(CH$_2$SiH$_2$CH$_2$), (organoamino)SiH(CH$_2$)$_2$SiH(organoamino), (organoamino)SiH$_2$Me, or (organoamino)SiH$_2$Ph. In certain embodiments, asymmetric imines could be used as a reagent in a reaction mixture comprising a silicon source in the presence of a catalyst to provide organoaminosilanes, organoaminodisilanes, or organoaminocarbosilanes having asymmetric organoamino groups. In this regard, these asymmetric organoamino precursors would otherwise have been unfeasible to synthesize using prior art methods due to scarcity of the corresponding amine [e.g. ($^s$Bu)($^i$Pr)NH, ($^t$Bu)($^i$Pr)NH].

The methods described herein provide a means to synthesize desirable compounds such as but not limited to organoaminosilanes (e.g., DIPAS), organoaminodisilanes (e.g., DIPADS), organoaminocarbosilanes, at relatively high yields. In this regard, exemplary yields obtainable for the compounds using the synthesis method described herein are 50 mol % or greater, 55 mol % or greater, 60 mol % or greater, 65 mol % or greater, 70 mol % or greater, 75 mol % or greater, 80 mol % or greater, or 90 mol % or greater based on the imine usage. In synthesis processes wherein the silicon source comprises a hydrosilane reagent having at least two Si—H groups, once one hydrosilylation has taken place at a single silicon atom, the rate for a second, third, or fourth hydrosilylation to take place at the same silicon atom becomes significantly and successively slower. In contrast, in synthesis processes involving reacting lithium-amides with Si—X$_n$ (X=halide or H, n=2,3,4) compounds, or when reacting primary or secondary amines with said compounds, preventing over-amination is difficult. Therefore, there is a kinetic selectivity for preparing compounds such as organoaminosilanes in a more subtle, less harsh hydrosilylation method such as the method described herein.

As previously discussed, an imine is reacted with a silicon source to form a reaction mixture comprising a compound such as without limitation, an organoaminosilane (e.g., DIPAS), an organoaminodisilanes (e.g., DIPADS), and organoaminocarbosilanes. In these embodiments, the silicon source reagent may include a hydridosilane having the formula of R$^1$R$^2$R$^3$SiH wherein R$^1$, R$^2$ and R$^3$ are each independently selected from hydrogen, a C$_{1-10}$ linear alkyl group, a C$_{3-10}$ branched alkyl group, a C$_{4-10}$ cyclic alkyl group, a C$_{2-10}$ alkenyl group, a C$_{4-10}$ aromatic group, a C$_{4-10}$ heterocyclic group, a C$_{1-10}$ linear organoamino group, a C$_{2-10}$ branched organoamino groups, a silyl group, a C$_{1-10}$ linear carbosilyl group, and a C$_{2-10}$ branched carbosilyl group and wherein at least one of R$^1$ and R$^2$, R$^1$ and R$^3$, or R$^2$ and R$^3$ or none of R$^1$ and R$^2$, R$^1$ and R$^3$, or R$^2$ and R$^3$ are linked to form a substituted or unsubstituted cyclic ring.

The imine reagents may include secondary aldimines, R—N=CHR', or secondary ketimines, R—N=CR'R", containing linear or branched organic R, R' and R" functionalities and wherein R, R' and R" are as described herein, though it is preferable that alkyl functionalities be sufficiently large to afford stability during purification processes and storage of the final organoaminosilane product. Exemplary imines include, but are not limited to, N-iso-propyl-iso-propylidenimine, N-iso-propyl-sec-butylidenimine, N-sec-butyl-sec-butylidenimine, and N-tert-butyl-iso-propylidineimine.

The molar ratio of imine to the hydridosilane in the reaction mixture ranges from 1 to 0.5, 1 to 1, 2 to 1, 3 to 1, 5 to 1, or from 10 to 1. In embodiments wherein the hydridosilane reagent comprises only one or two Si—H bonds per silicon atom, the reaction may yield solely the singly substituted amine derivative and be insensitive to higher imine ratios, especially if the imine has large substituents. In embodiments wherein the hydridosilane reagent in the reaction mixture comprises three or more Si—H bonds per silicon atom, an excess of hydridosilane is used to avoid bis(amino)silane products. In some embodiments, the hydridosilane has only one Si—H$_x$ group, wherein x is a number ranging from 1 to 4, such as silane, methylsilane, diethylsilane, or trimethylsilane. In other embodiments, wherein the hydridosilane has more than one Si—H$_x$ groups, wherein x is a number ranging from 1 to 3, such as disilane, 1,4-disilabutane, or polysilanes, an excess of hydridosilane is used if the desired organoaminodisilane or organoaminocarbosilane product is to have only one organoamino group. In one particular embodiment, the reaction mixture has a 1:2.2 to 1:2.3 molar ratio of imine to hydridosilane to ensure the reaction proceeds quickly to completion and to prevent more than one hydrosilylation reaction per hydridosilane molecule.

The molar ratio of catalyst to imine in the reaction mixture ranges from 0.1 to 1, 0.05 to 1, 0.01 to 1, 0.005 to 1, 0.001 to 1, 0.0005 to 1, 0.0001 to 1, 0.00005 to 1, or 0.00001 to 1. In one particular embodiment 0.05 to 0.07 equivalents of catalyst is used per equivalent of imine. In another particular embodiment 0.00008 equivalents of catalyst is used per equivalent of imine.

In certain embodiments, the reaction mixture comprising the hydridosilane reagent(s), imine reagent(s), and catalyst(s) further comprises an anhydrous solvent. Exemplary solvents may include, but are not limited to linear-, branched-, cyclic-, or poly-ethers (e.g., tetrahydrofuran (THF), diethyl ether, diglyme, and/or tetraglyme); linear-, branched-, or cyclic-alkanes, alkenes, aromatics and halocarbons (e.g. pentane, hexanes, toluene and dichloromethane). The selection of one or more solvent, if added, may be influenced by its compatibility with reagents contained within the reaction mixture, the solubility of the catalyst, and/or the separation process for the intermediate product and/or the end product chosen. In other embodiments, the reaction mixture does not comprise a solvent. In these or other embodiments, the mixture of imine and hydridosilane reagents may be used as the liquid medium for the reaction in the reaction mixture. In alternative embodiments, however, the reaction mixture does not contain any solvent.

In the method described herein, the reaction between the hydridosilane reagent(s) and the imine reagent(s) occurs at one or more temperatures ranging from about 0° C. to about 100° C. Exemplary temperatures for the reaction include ranges having any one or more of the following endpoints: 0, 10, 20, 30, 40, 50, 60, 70, 80, 90, or 100° C. The suitable temperature range for this reaction may be dictated by the physical properties of the hydridosilane reagent(s), imine reagent(s), catalyst(s), and optional solvent. Examples of particular reactor temperature ranges include but are not limited to, 0° C. to 80° C. or from 0° C. to 30° C.

In certain embodiments of the method described herein, the pressure of the reaction may range from about 1 to about 115 psia or from about 15 to about 45 psia. In some embodiments where the hydridosilane reagent is a liquid under ambient conditions, the reaction is run at atmospheric pressure. In some embodiments where the hydridosilane reagent is a gas under ambient conditions, the reaction is run under above 15 psia.

In certain embodiments, one or more reagents may be introduced to the reaction mixture as a liquid or a vapor. In embodiments where one or more of the reagents is added as a vapor, a non-reactive gas such as nitrogen or an inert gas may be employed as a carrier gas to deliver the vapor to the reaction mixture. In embodiments where one or more of the reagents is added as a liquid, the regent may be added neat, or alternatively diluted with a solvent. The reagent is fed to the reaction mixture until the desired conversion to the crude mixture containing the organoaminosilane product, or crude liquid, has been achieved. In certain embodiments, the reaction may be run in a continuous manner by replenishing the hydridosilane and/or imine reagents and removing the reaction products and the crude liquid from the reactor.

An example of the catalytic hydrosiliation method described herein comprises a combining hydridosilane and imine to provide a reaction mixture in the presence of 0.1-10 mol % catalyst under ambient conditions to produce an organoaminosilane, organoaminodisilane, or organoaminocarbosilane compound as shown below in the following reaction scheme (1). The hydridosilane reagent having the following formula $R^1R^2R^3SiH$ wherein $R^1$, $R^2$ and $R^3$ are each independently selected from hydrogen, $C_{1-10}$ linear alkyl group, a $C_{3-10}$ branched alkyl group, a $C_{4-10}$ cyclic alkyl group, a $C_{2-10}$ alkenyl group, a $C_{4-10}$ aromatic group, a $C_{4-10}$ heterocyclic group, a $C_{1-10}$ linear organoamino group, a $C_{2-10}$ branched organoamino groups, a silyl group, a $C_{1-10}$ linear carbosilyl group, and a $C_{2-10}$ branched carbosilyl group and wherein at least one of, or none of, $R^1$ and $R^2$, $R^1$ and $R^3$, or $R^2$ and $R^3$ in the hydridosilane reagent are linked to form a substituted or unsubstituted cyclic ring.

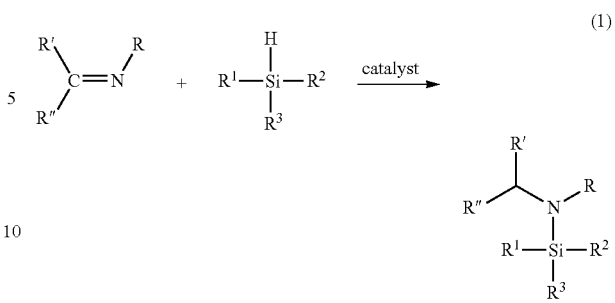

The reaction may require an excess of either hydridosilane reagent or imine to regulate the extent of hydrosilylation, and solvents such as tetrahydrofuran (THF) or hexanes may be used to facilitate the reaction progress. The hydridosilane reagents that are volatile liquids or gases [e.g. $SiH_4$ (silane), $Si_2H_6$ (disilane), $MeSiH_3$ (methylsilane), $EtSiH_3$ (ethylsilane), $Et_2SiH_2$ (diethylsilane), $PhSiH_3$ (phenylsilane), $H_3SiCH_2CH_2SiH_3$ (1,4-disilabutane), $H_3SiCH_2SiH_3$ (1,3-disilapropane), $H_3SiCH_2(CH_3)SiH_3$ (2-methyl-1,4-disilapropane), $(CH_2CH_2CH_2CH_2)SiH_2$ (1-silacyclopentane), $(CH_2CH_2CH_2CH_2)SiHMe$ (1-methyl-1-silacyclopentane), $(CH_2CH_2CH_2)SiH_2$ (1-silacyclobutane), $(CH_2SiH_2CH_2)SiH_2$ (1,3-disilacyclobutane)], pressures greater than 1 atmospheres (atm) may be required to maintain sufficient levels of these reagents in the liquid phase. Once the reaction is complete or has reached equilibrium, the organoaminosilane, organoaminodisilane, or organoaminocarbosilane product can be purified by distillation. Referring to the above reaction scheme (1), the final organoaminosilane, organoaminodisilane, or organoaminocarbosilane product is formed by the reaction of the imine and hydridosilane. A >50% stoichiometric excess of hydridosilane is generally used to ensure complete reaction, though smaller excesses may be used if the mixing period is adequately long The crude mixture comprising the desired organoaminosilane, organoaminodisilane, or organoaminocarbosilane product, catalyst(s), and potentially residual imine, residual hydridosilane, solvent(s), or undesired organoaminosilane product(s) may require separation process(es). Examples of suitable separation processes include, but are not limited to, distillation, evaporation, membrane separation, filtration, vapor phase transfer, extraction, fractional distillation using an inverted column, and combinations thereof. In particular embodiments, the crude fluid is first separated from the residual catalyst by vacuum transfer or distillation at lower temperatures prior to isolation of the desired product by fractional distillation in order to prevent the catalyzation of undesired reactions during the purification process. In these embodiments, the pressure can vary considerably from atmospheric to full vacuum. In this embodiment or other embodiments, the reaction occurs at one or more temperatures ranging from about 20° C. to about 200° C. Exemplary temperatures for the reaction include ranges having any one or more of the following endpoints: 20, 30, 40, 50, 60, 70, 80, 90, 100, 110, 120, 130, 140, 150, 160, 170, 180, 190, or 200° C. Examples of particular reactor temperature ranges include but are not limited to, 20° C. to 200° C. or from 70° C. to 160° C.

In certain embodiments of the method described herein, the pressure of the reaction may range from about 0.1 to about 115 psia or from about 10 to about 45 psia. In one particular embodiment, the reaction is run at a pressure of about 100 psia.

In certain preferred embodiments, the reagents in the reaction mixture are gaseous. In these embodiments, the contact of the catalyst with reaction mixture may be defined in terms of defined by the bulk reactor volume displaced by the catalyst÷ reactant (e.g., silane and/or silica source gas) gas flow rate. The gas-catalyst contact time may range from about 5 to about 200 seconds. Exemplary times for the contact of the reactive mixture with the catalyst include ranges having any one or more of the following endpoints: 5, 10, 20, 30, 40, 50, 60, 70, 80, 90, 100, 110, 120, 130, 140, 150, 160, 170, 180, 190, or 200 seconds. Examples of particular contact time ranges include but are not limited to, 20 to 100 or from 10 to 40 seconds.

Exemplary catalysts that can be used with the method described herein include, but are not limited to the following: alkaline earth metal catalysts; halide-free main group, transition metal, lanthanide, and actinide catalysts; and halide-containing main group, transition metal, lanthanide, and actinide catalysts.

Exemplary alkaline earth metal catalysts include but are not limited to the following: $Mg[N(SiMe_3)_2]_2$, $To^M MgMe$ [$To^M$=tris(4,4-dimethyl-2-oxazolinyl)phenylborate], $To^M Mg$—H, $To^M Mg$—$NR_2$ (R=H, alkyl, aryl) $Ca[N(SiMe_3)_2]_2$, [(dipp-nacnac)CaX(THF)]$_2$ (dipp-nacnac=CH[(CMe)(2,6-$^i Pr_2$-$C_6 H_3$N)]$_2$; X=H, alkyl, carbosilyl, organoamino), $Ca(CH_2 Ph)_2$, $Ca(C_3 H_5)_2$, $Ca(\alpha$-$Me_3 Si$-$2$-$(Me_2 N)$-benzyl)$_2$(THF)$_2$, $Ca(9$-$(Me_3 SO$-fluorenyl)($\alpha$-$Me_3 Si$-$2$-$(Me_2 N)$-benzyl)(THF), $[(Me_3 TACD)_3 Ca_3 (\mu^3$-H)$_2]^+$ ($Me_3 TACD=Me_3[12]aneN_4$), $Ca(\eta^2$-$Ph_2 CNPh)(hmpa)_3$ (hmpa=hexamethylphosphoramide), $Sr[N(SiMe_3)_2]_2$, and other $M^{2+}$ alkaline earth metal-amide, -imine, -alkyl, -hydride, and -carbosilyl complexes (M=Ca, Mg, Sr, Ba).

Exemplary halide-free, main group, transition metal, lanthanide, and actinide catalysts include but are not limited to the following: 1,3-diisopropyl-4,5-dimethylimidazol-2-ylidene, 2,2'-bipyridyl, phenanthroline, $B(C_6 F_5)_3$, $BR_3$ (R=linear, branched, or cyclic $C_1$ to $C_{10}$ alkyl group, a $C_5$ to $C_{10}$ aryl group, or a $C_1$ to $C_{10}$ alkoxy group), $AlR_3$ (R=linear, branched, or cyclic $C_1$ to $C_{10}$ alkyl group, a $C_5$ to $C_{10}$ aryl group, or a $C_1$ to $C_{10}$ alkoxy group), $(C_5 H_5)_2 TiR_2$ (R=alkyl, H, alkoxy, organoamino, carbosilyl), $(C_5 H_5)_2 Ti(OAr)_2$ [Ar=(2,6-($^i Pr)_2 C_6 H_3$)], $(C_5 H_5)_2 Ti(SiHRR')PMe_3$ (wherein R, R' are each independently selected from H, Me, Ph), $TiMe_2$(dmpe)$_2$ (dmpe=1,2-bis(dimethylphosphino)ethane), bis(benzene)chromium(0), $Cr(CO)_6$, $Mn_2(CO)_{12}$, $Fe(CO)_5$, $Fe_3(CO)_{12}$, $(C_5 H_5)Fe(CO)_2 Me$, $Co_2(CO)_8$, Ni(II) acetate, Nickel (II) acetylacetonate, Ni(cyclooctadiene)$_2$, [(dippe)Ni($\mu$-H)]$_2$ (dippe=1,2-bis(diisopropylphosphino)ethane), (R-indenyl)Ni(PR'$_3$)Me (R=1-$^i Pr$, 1-$SiMe_3$, 1,3-($SiMe_3)_2$; R'=Me,Ph), [{Ni($\eta$-$CH_2$:CHSiMe$_2$)$_2$O}$_2${$\mu$-($\eta$-$CH_2$:CHSiMe$_2$)$_2$O}], Cu(I) acetate, CuH, [tris(4,4-dimethyl-2-oxazolinyl)phenylborate]ZnH, $(C_5 H_5)_2 ZrR_2$ (R=alkyl, H, alkoxy, organoamino, carbosilyl), $Ru_3(CO)_{12}$, [($Et_3 P$)Ru(2,6-dimesitylthiophenolate)][B[3,5-($CF_3)_2 C_6 H_3]_4$], [($C_5 Me_5$)Ru($R_3 P$)$_x$(NCMe)$_{3-x}$]$^+$ (wherein R is selected from a linear, branched, or cyclic $C_1$ to $C_{10}$ alkyl group and a $C_5$ to $C_{10}$ aryl group; x=0, 1, 2, 3), $Rh_6(CO)_{16}$, tris(triphenylphosphine)rhodium(I)carbonyl hydride, $Rh_2 H_2(CO)_2(dppm)_2$ (dppm=bis(diphenylphosphino)methane, $Rh_2(\mu$-SiRH)$_2$(CO)$_2$(dppm)$_2$ (R=Ph, Et, $C_6 H_{13}$), Pd/C, tris(dibenzylideneacetone)dipalladium(0), tetrakis(triphenylphosphine)palladium(0), Pd(II) acetate, $(C_5 H_5)_2 SmH$, $(C_5 Me_5)_2 SmH$, $(THF)_2 Yb[N(SiMe_3)_2]_2$, (NHC)Yb(N(SiMe$_3$)$_2$)$_2$ [NHC=1,3-bis(2,4,6-trimethylphenyl) imidazol-2-ylidene)], $Yb(\eta^2$-$Ph_2 CNPh)(hmpa)_3$ (hmpa=hexamethylphosphoramide), $W(CO)_6$, $Re_2(CO)_{10}$, $Os_3(CO)_{12}$, $Ir_4(CO)_{12}$, (acetylacetonato)dicarbonyliridium (I), $Ir(Me)_2(C_5 Me_5)L$ (L=$PMe_3$, $PPh_3$), [Ir(cyclooctadiene) OMe]$_2$, $PtO_2$ (Adams's catalyst), Pt/C, Platinum(0)-1,3-divinyl-1,1,3,3-tetramethyldisiloxane (Karstedt's catalyst), bis(tri-tert-butylphosphine)platinum(0), Pt(cyclooctadiene)$_2$, [(Me$_3$Si)$_2$N]$_3$U][BPh$_4$], [(Et$_2$N)$_3$U][BPh$_4$], and other halide-free $M^{n+}$ complexes (M=Sc, Ti, V, Cr, Mn, Fe, Co, Ni, Cu, Zn, Y, Zr, Nb, Mo, Ru, Rh, Pd, La, Ce, Pr, Nd, Pm, Sm, Eu, Gd, Tb, Dy, Ho, Er, Tm, Yb, Lu, Hf, Ta, W, Re, Os, Ir, Pt, U; n=0, 1, 2, 3, 4, 5, 6).

Exemplary halide-containing, main group, transition metal, lanthanide, and actinide catalysts include but are not limited to the following: $BX_3$ (X=F, Cl, Br, I), $BF_3 \cdot OEt_2$, $AlX_3$ (X=F, Cl, Br, I), $(C_5 H_5)_2 TiX_2$ (X=F, Cl), [Mn(CO)$_4$Br]$_2$, $NiCl_2$, $(C_5 H_5)_2 ZrX_2$ (X=F, Cl), $PdCl_2$, $PdI_2$, CuCl, CuI, $CuF_2$, $CuCl_2$, $CuBr_2$, $Cu(PPh_3)_3 Cl$, $ZnCl_2$, [(C$_6$H$_6$)RuX$_2$]$_2$ (X=Cl, Br, I), (Ph$_3$P)$_3$RhCl (Wilkinson's catalyst), [RhCl(cyclooctadiene)]$_2$, di-$\mu$-chloro-tetracarbonyldirhodium(I), bis(triphenylphosphine)rhodium(I) carbonyl chloride, $NdI_2$, $SmI_2$, $DyI_2$, (POCOP)IrHCl (POCOP=2,6-(R$_2$PO)$_2$C$_6$H$_3$; R=$^i Pr$, $^n Bu$, Me), $H_2 PtCl_6 \cdot nH_2 O$ (Speier's catalyst), $PtCl_2$, $Pt(PPh_3)_2 Cl_2$, and other halide-containing $M^{n+}$ complexes (M=Sc, Ti, V, Cr, Mn, Fe, Co, Ni, Cu, Zn, Y, Zr, Nb, Mo, Ru, Rh, Pd, La, Ce, Pr, Nd, Pm, Sm, Eu, Gd, Tb, Dy, Ho, Er, Tm, Yb, Lu, Hf, Ta, W, Re, Os, Ir, Pt, U; n=0, 1, 2, 3, 4, 5, 6).

In certain embodiments, the compounds, or organoaminosilanes, organoaminodisilanes, and organoaminocarbosilanes, prepared using the methods described herein and compositions comprising the compounds are preferably substantially free of halide ions. As used herein, the term "substantially free" as it relates to halide ions (or halides) such as, for example, chlorides and fluorides, bromides, and iodides, means less than 5 ppm (by weight), preferably less than 3 ppm, and more preferably less than 1 ppm, and most preferably 0 ppm. Compositions according to the present invention that are substantially free of halides can be achieved by (1) reducing or eliminating chloride sources during chemical synthesis, and/or (2) implementing an effective purification process to remove chloride from the crude product such that the final purified product is substantially free of halides. Halide sources may be reduced during synthesis by using reagents that do not contain halides such as the halide-free catalysts described herein. In a similar manner, the synthesis should not use halide based solvents, catalysts, or solvents which contain unacceptably high levels of halide contamination. Alternatively, or additionally, the crude product may also be treated by various purification methods to render the final product substantially free of halides such as chlorides. Such methods are well described in the prior art and, may include, but are not limited to, purification processes such as distillation, or adsorption. Distillation is commonly used to separate impurities from the desire product by exploiting differences in boiling point. Adsorption may also be used to take advantage of the differential adsorptive properties of the components to effect separation such that the final product is substantially free of halide. Adsorbents such as, for example, commercially available solid bases can be used to remove halides such as chloride.

The following Table 1 lists imines that can be used as reagents in the method described herein to provide exemplary organoaminosilanes, organoaminodisilanes, organoaminocarbosilanes, and organoamines compounds defined herein.

TABLE 1

Exemplary imines

| | | | |
|---|---|---|---|
| N-iso-propylidene-methylamine | N-sec-butylidene-methylamine | N-cyclohexylidene-methylamine | N-cyclopentylidene-methylamine |
| N-iso-propylidene-ethylamine | N-sec-butylidene-ethylamine | N-cyclohexylidene-ethylamine | N-cyclopentylidene-ethylamine |
| N-iso-propylidene-n-propylamine | N-sec-butylidene-n-propylamine | N-cyclohexylidene-n-propylamine | N-cyclopentylidene-n-propylamine |
| N-iso-propylidene-iso-propylamine | N-sec-butylidene-iso-propylamine | N-cyclohexylidene-iso-propylamine | N-cyclopentylidene-iso-propylamine |
| N-iso-propylidene-sec-butylamine | N-sec-butylidene-sec-butylamine | N-cyclohexylidene-sec-butylamine | N-cyclopentylidene-sec-butylamine |
| N-iso-propylidene-tert-butylamine | N-sec-butylidene-tert-butylamine | N-cyclohexylidene-tert-butylamine | N-cyclopentylidene-tert-butylamine |
| N-iso-propylidene-cyclohexylamine | N-sec-butylidene-cyclohexylamine | N-cyclohexylidene-cyclohexylamine | N-cyclopentylidene-cyclohexylamine |
| N-iso-propylidene-phenylamine | N-sec-butylidene-phenylamine | N-cyclohexylidene-phenylamine | N-cyclopentylidene-phenylamine |
| N-ethylidene-phenylamine | N-methylidene-methylamine | N-ethylidene-ethylamine | N-n-propylidene-n-propylamine |

TABLE 2

Exemplary Organoaminosilane Compounds

| N-methyl-N-iso-propylaminosilane | N-sec-butyl-N-methylaminosilane | N-cyclohexyl-N-methylaminosilane | N-methyl-N-cyclopentylaminosilane |
| N-ethyl-N-iso-propylaminosilane | N-sec-butyl-N-ethylaminosilane | N-ethyl-N-cyclohexylaminosilane | N-ethyl-N-cyclopentylaminosilane |
| N-n-propyl-N-iso-propylaminosilane | N-sec-butyl-N-n-propylaminosilane | N-cyclohexyl-N-n-propylaminosilane | N-cyclopentyl-N-n-propylaminosilane |
| N,N-di-iso-propylaminosilane | N-sec-butyl-N-iso-propylaminosilane | N-cyclohexyl-N-iso-propylaminosilane | N-cyclopentyl-N-iso-propylaminosilane |
| N,N-di-sec-butylaminosilane | N-sec-butyl-N-cyclohexylaminosilane | N-sec-butyl-N-cyclopentylaminosilane | N-tertbutyl-N-iso-propylaminosilane |
| N-sec-butyl-N-tert-butylaminosilane | N-tert-butyl-N-cyclohexylaminosilane | N-tert-butyl-N-cyclopentylaminosilane | N,N-dicyclohexyl-aminosilane |
| N-cyclohexyl-N-cyclopentylaminosilane | N-phenyl-N-iso-propylaminosilane | N-sec-butyl-N-phenylaminosilane | N-cyclohexyl-N-phenylaminosilane |
| N-cyclopentyl-N- | N-ethyl-N- | N,N-dimethylaminosilane | N,N-diethylaminosilane |

TABLE 2-continued

Exemplary Organoaminosilane Compounds

| phenylaminosilane | phenylaminosilane |
|---|---|
| 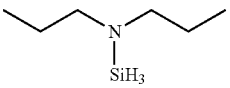 N,N-di-n-propylaminosilane | |

TABLE 3

Exemplary Organoaminodisilane Compounds

|  | 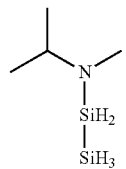 | 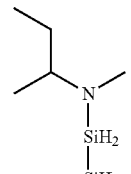 | 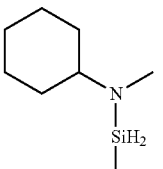 |
|---|---|---|---|
| N-methyl-N-iso-propylaminodisilane | N-sec-butyl-N-methylaminodisilane | N-cyclohexyl-N-methylaminodisilane | N-methyl-N-cyclopentylaminodisilane |
| 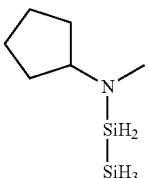 | 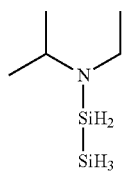 | 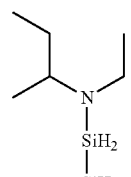 | 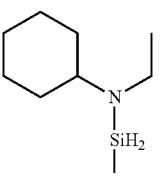 |
| N-ethyl-N-iso-propylaminodisilane | N-sec-butyl-N-ethylaminodisilane | N-ethyl-N-cyclohexylaminodisilane | N-ethyl-N-cyclopentylaminodisilane |
| 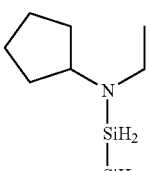 | 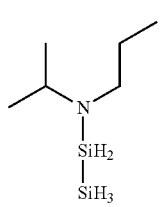 | 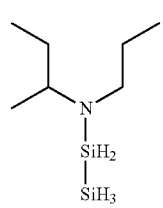 | 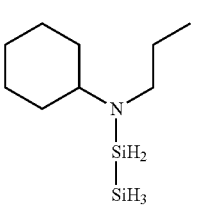 |
| N-n-propyl-N-iso-propylaminodisilane | N-sec-butyl-N-n-propylaminodisilane | N-cyclohexyl-N-n-propylaminodisilane | N-cyclopentyl-N-n-propylaminodisilane |
| 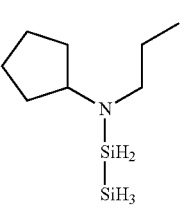 | 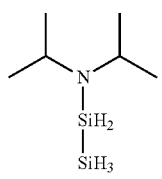 | 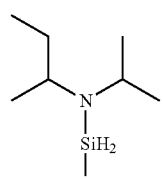 | 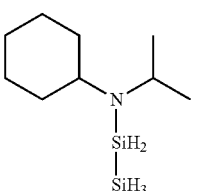 |
| N,N-di-iso-propylaminodisilane | N-sec-butyl-N-iso-propylaminodisilane | N-cyclohexyl-N-iso-propylaminodisilane | N-cyclopentyl-N-iso-propylaminodisilane |
| 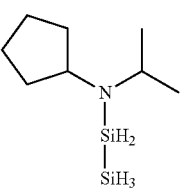 | 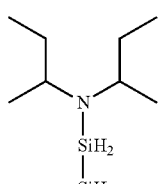 | 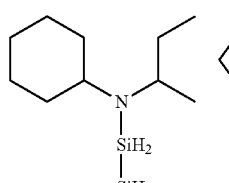 | 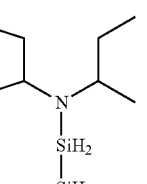 |
| N,N-di-sec-butylaminodisilane | N-sec-butyl-N-cyclohexylaminodisilane | N-sec-butyl-N-cyclopentylaminodisilane | N-tert-butyl-N-iso-propylaminodisilane |

TABLE 3-continued

Exemplary Organoaminodisilane Compounds

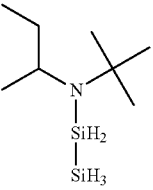 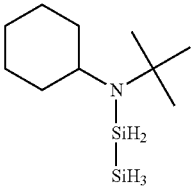 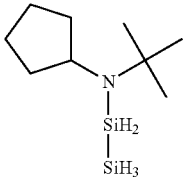 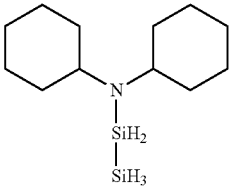

N-sec-butyl-N-tert-butylaminodisilane | N-tert-butyl-N-cyclohexylaminodisilane | N-tert-butyl-N-cyclopentylaminodisilane | N,N-dicyclohexyl-aminodisilane

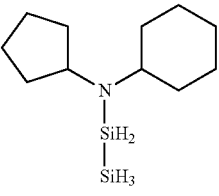 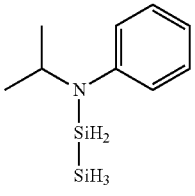 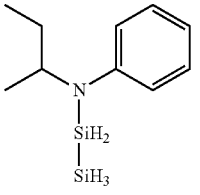 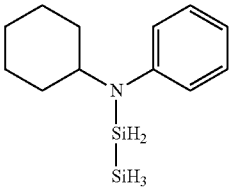

N-cyclohexyl-N-cyclopentylaminodisilane | N-phenyl-N-iso-propylaminodisilane | N-sec-butyl-N-phenylaminodisilane | N-cyclohexyl-N-phenylaminodisilane

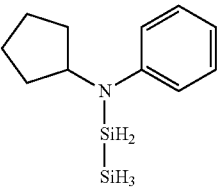 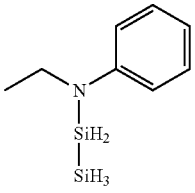 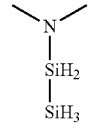 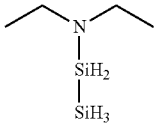

N-cyclopentyl-N-phenylaminodisilane | N-ethyl-N-phenylaminodisilane | N,N-dimethyl-aminodisilane | N,N-diethyl-aminodisilane

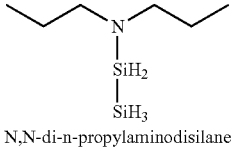

N,N-di-n-propylaminodisilane

TABLE 4

Exemplary Organoaminodisilane (more specifically 1,2-bis(organoamino)disilane) Compounds

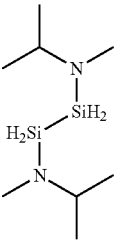 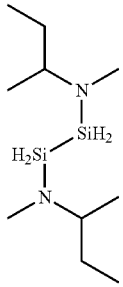 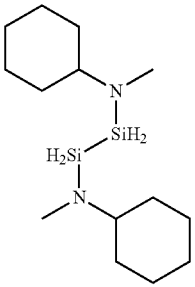 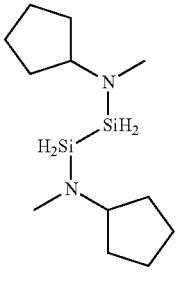

1,2-bis(N-methyl-N-iso-propylamino)disilane | 1,2-bis(N-sec-butyl-N-methylamino)disilane | 1,2-bis(N-cyclohexyl-N-methylamino)disilane | 1,2-bis(N-methyl-N-cyclopentylamino)disilane TABLE 4-continued Exemplary Organoaminodisilane (more specifically 1,2-bis(organoamino)disilane) Compounds

| 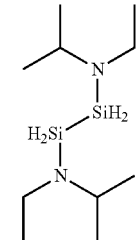 | 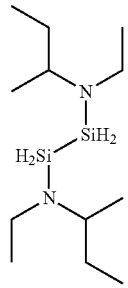 | 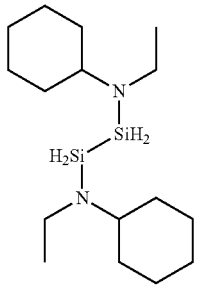 | 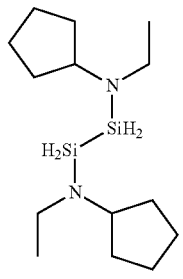 |
|---|---|---|---|
| 1,2-bis(N-ethyl-N-iso-propylamino)disilane | 1,2-bis(N-sec-butyl-N-ethylamino)disilane | 1,2-bis(N-ethyl-N-cyclohexylamino)disilane | 1,2-bis(N-ethyl-N-cyclopentylamino)disilane |
| 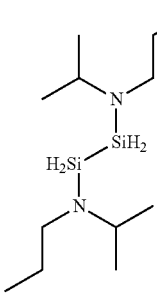 | 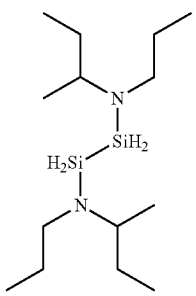 | 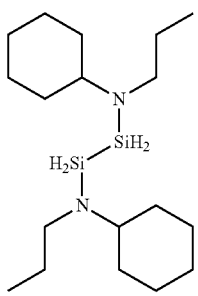 | 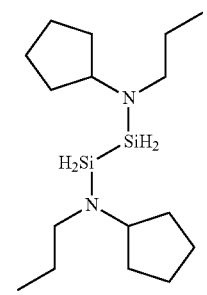 |
| 1,2-bis(N-n-propyl-N-iso-propylamino)disilane | 1,2-bis(N-sec-butyl-N-n-propylamino)disilane | 1,2-bis(N-cyclohexyl-N-n-propylamino)disilane | 1,2-bis(N-cyclopentyl-N-n-propylamino)disilane |
| 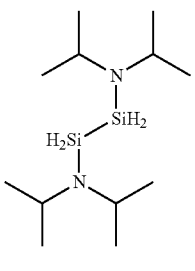 | 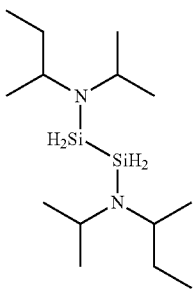 | 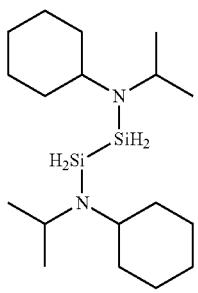 | 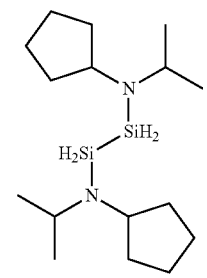 |
| 1,2-bis(N,N-di-iso-propylamino)disilane | 1,2-bis(N-sec-butyl-N-iso-propylamino)disilane | 1,2-bis(N-cyclohexyl-N-iso-propylamino)disilane | 1,2-bis(N-cyclopentyl-N-iso-propylamino)disilane |
| 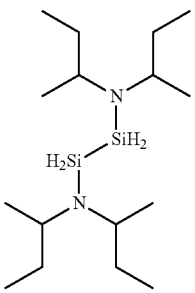 | 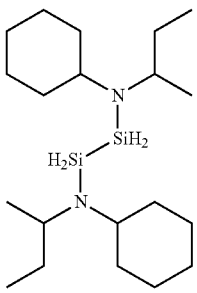 | 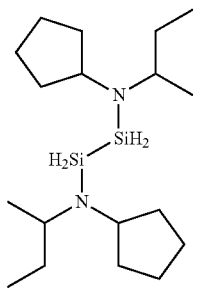 | 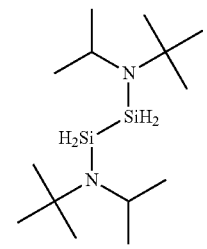 |
| 1,2-bis(N,N-di-sec-butylamino)disilane | 1,2-bis(N-sec-butyl-N-cyclohexylamino)disilane | 1,2-bis(N-sec-butyl-N-cyclopentylamino)disilane | 1,2-bis(N-tert-butyl-N-iso-propylamino)disilane |

TABLE 4-continued

Exemplary Organoaminodisilane (more specifically 1,2-bis(organoamino)disilane) Compounds

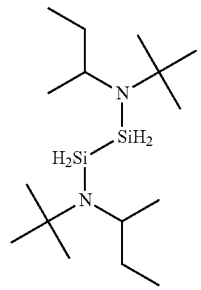 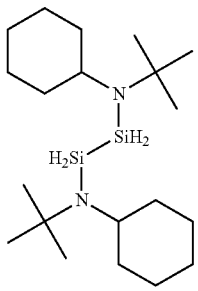 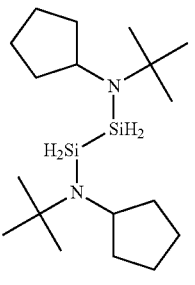 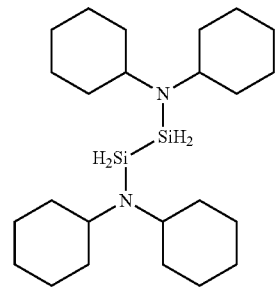

| 1,2-bis(N-sec-butyl-N-tert-butylamino)disilane | 1,2-bis(N-tert-butyl-N-cyclohexylamino)disilane | 1,2-bis(N-tert-butyl-N-cyclopentylamino)disilane | 1,2-bis(N,N-diclohexylamino)disilane |

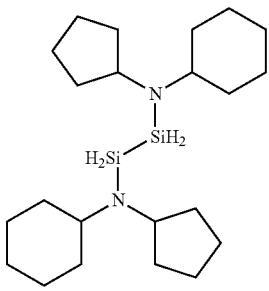 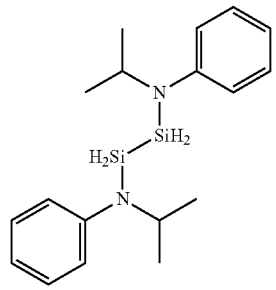 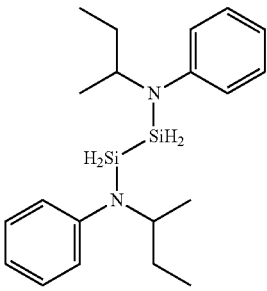 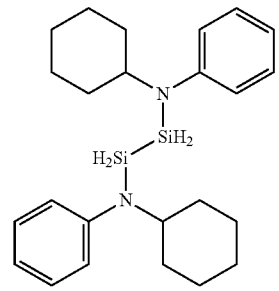

| 1,2-bis(N-cyclohexyl-N-cyclopentylamino)disilane | 1,2-bis(N-phenyl-N-iso-propylamino)disilane | 1,2-bis(N-sec-butyl-N-phenylamino)disilane | 1,2-bis(N-cyclohexyl-N-phenylamino)disilane |

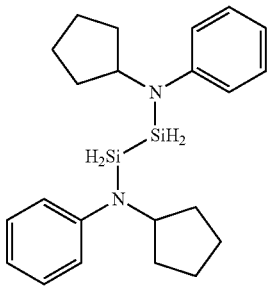 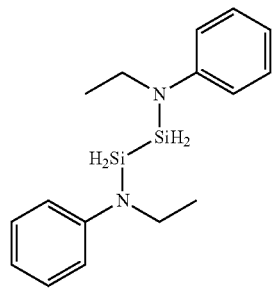 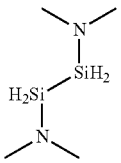 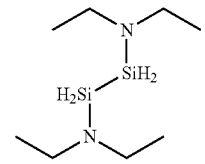

| 1,2-bis(N-cyclopentyl-N-phenylamino)disilane | 1,2-bis(N-ethyl-N-phenylamino)disilane | 1,2-bis(N,N-dimethylamino)disilane | 1,2-bis(N,N-dieethylamino)disilane |

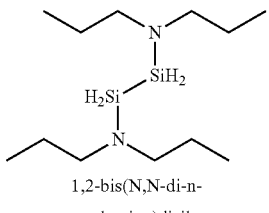

1,2-bis(N,N-di-n-propylamino)disilane

TABLE 5

Exemplary Organoaminocarbosilane (more specifically organoamino-1,4-disilabutane) Compounds

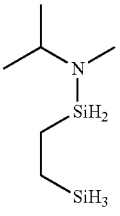
1-(N-methyl-N-iso-propylamino)-1,4-disilabutane

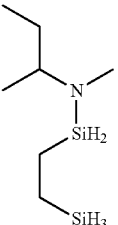
1-(N-sec-butyl-N-methylamino)-1,4-disilabutane

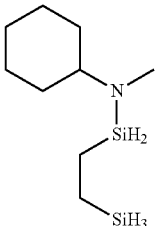
1-(N-cyclohexyl-N-methylamino)-1,4-disilabutane

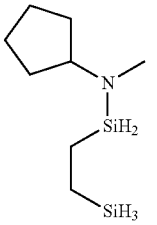
1-(N-methyl-N-cyclopentylamino)-1,4-disilabutane

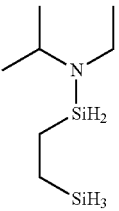
1-(N-ethyl-N-iso-propylamino)-1,4-disilabutane

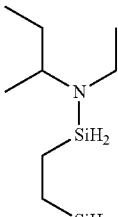
1-(N-sec-butyl-N-ethylamino)-1,4-disilabutane

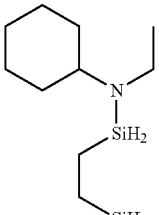
1-(N-ethyl-N-cyclohexylamino)-1,4-disilabutane

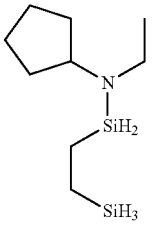
1-(N-ethyl-N-cyclopentylamino)-1,4-disilabutane

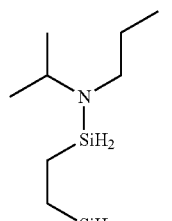
1-(N-n-propyl-N-iso-propylamino)-1,4-disilabutane

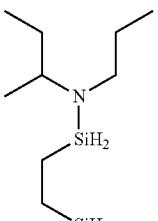
1-(N-sec-butyl-N-n-propylamino)-1,4-disilabutane

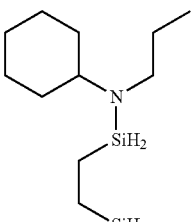
1-(N-cyclohexyl-N-n-propylamino)-1,4-disilabutane

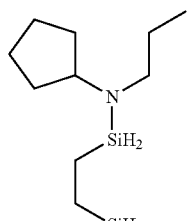
1-(N-cyclopentyl-N-n-propylamino)-1,4-disilabutane

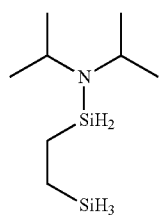
1-(N,N-di-iso-propylamino)-1,4-disilabutane

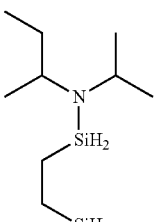
1-(N-sec-butyl-N-iso-propylamino)-1,4-disilabutane

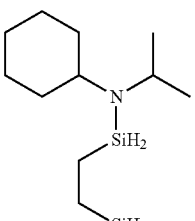
1-(N-cyclohexyl-N-iso-propylamino)-1,4-disilabutane

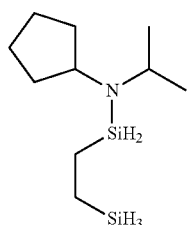
1-(N-cyclopentyl-N-iso-propylamino)-1,4-disilabutane

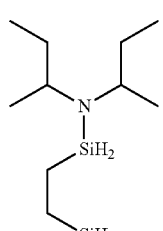
1-(N,N-di-sec-butylamino)-1,4-disilabutane

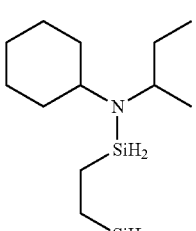
1-(N-sec-butyl-N-cyclohexylamino)-1,4-disilabutane

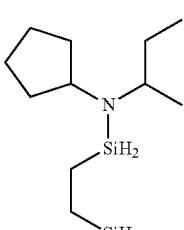
1-(N-sec-butyl-N-cyclopentylamino)-1,4-disilabutane

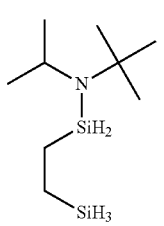
1-(N-tert-butyl-N-iso-propylamino)-1,4-disilabutane

TABLE 5-continued

Exemplary Organoaminocarbosilane (more specifically organoamino-1,4-disilabutane) Compounds

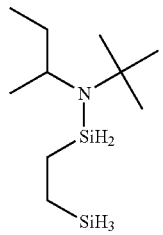 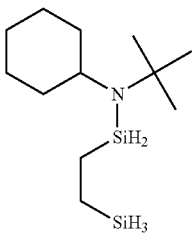 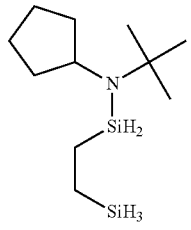 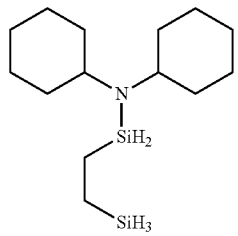

1-(N-sec-butyl-N-tert-butylamino)-1,4-disilabutane | 1-(N-tert-butyl-N-cyclohexylamino)-1,4-disilabutane | 1-(N-tert-butyl-N-cyclopentylamino)-1,4-disilabutane | 1-(N,N-dicyclohexylamino)-1,4-disilabutane

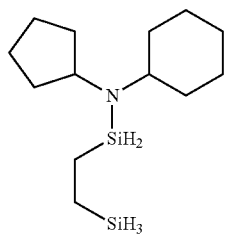 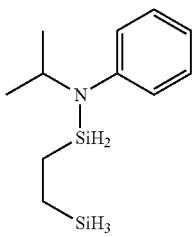 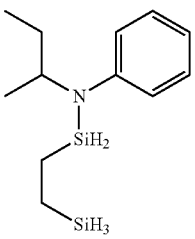 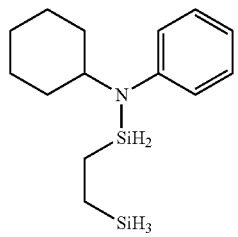

1-(N-cyclohexyl-N-cyclopentylamino)-1,4-disilabutane | 1-(N-phenyl-N-iso-propylamino)-1,4-disilabutane | 1-(N-sec-butyl-N-phenylamino)-1,4-disilabutane | 1-(N-cyclohexyl-N-phenylamino)-1,4-disilabutane

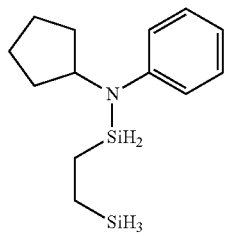 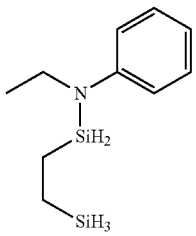 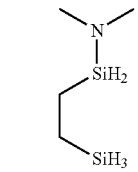 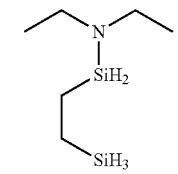

1-(N-cyclopentyl-N-phenylamino)-1,4-disilabutane | 1-(N-ethyl-N-phenylamino)-1,4-disilabutane | 1-(N,N-dimethylamino)-1,4-disilabutane | 1-(N,N-diethylamino)-1,4-disilabutane

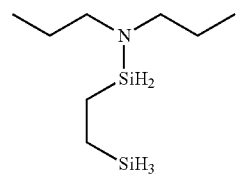

1-(N,N-di-n-propylamino)-1,4-disilabutane

TABLE 6

Exemplary Organoaminocarbosilane (more specifically 1,4-bis(organoamino)-1,4-disilabutane) Compounds

| 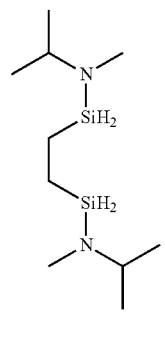 | 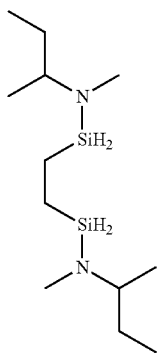 | 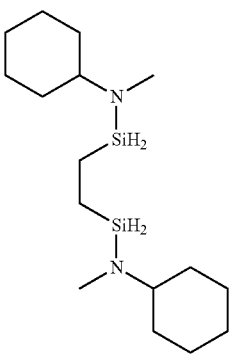 | 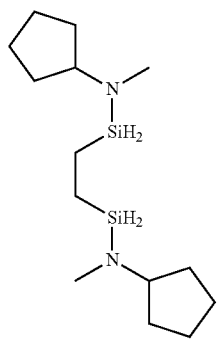 |
|---|---|---|---|
| 1,4-bis(N-methyl-N-iso-propylamino)-1,4-disilabutane | 1,4-bis(N-sec-butyl-N-methylamino)-1,4-disilabutane | 1,4-bis(N-cyclohexyl-N-methylamino)-1,4-disilabutane | 1,4-bis(N-methyl-N-cyclopentylamino)-1,4-disilabutane |
| 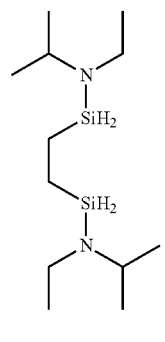 | 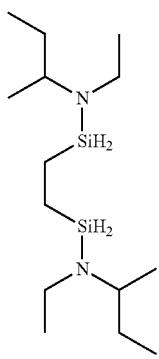 | 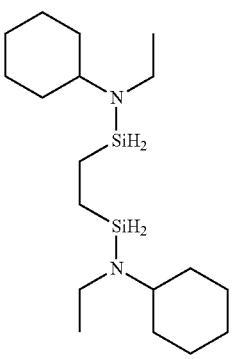 | 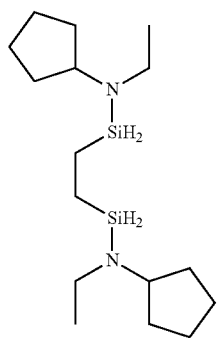 |
| 1,4-bis(N-ethyl-N-iso-propylamino)-1,4-disilabutane | 1,4-bis(N-sec-butyl-N-ethylamino)-1,4-disilabutane | 1,4-bis(N-ethyl-N-cyclohexylamino)-1,4-disilabutane | 1,4-bis(N-ethyl-N-cyclopentylamino)-1,4-disilabutane |
| 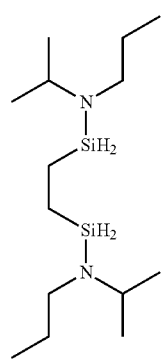 | 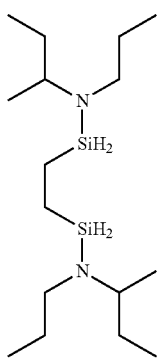 | 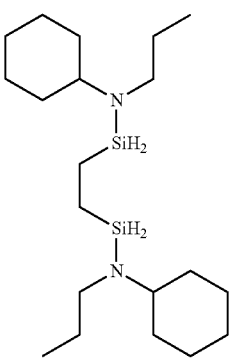 | 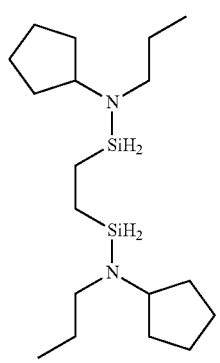 |
| 1,4-bis(N-n-propyl-N-iso-propylamino)-1,4-disilabutane | 1,4-bis(N-sec-butyl-N-n-propylamino)-1,4-disilabutane | 1,4-bis(N-cyclohexyl-N-n-propylamino)-1,4-disilabutane | 1,4-bis(N-cyclopentyl-N-n-propylamino)-1,4-disilabutane |

TABLE 6-continued
Exemplary Organoaminocarbosilane (more specifically 1,4-bis(organoamino)-1,4-disilabutane) Compounds
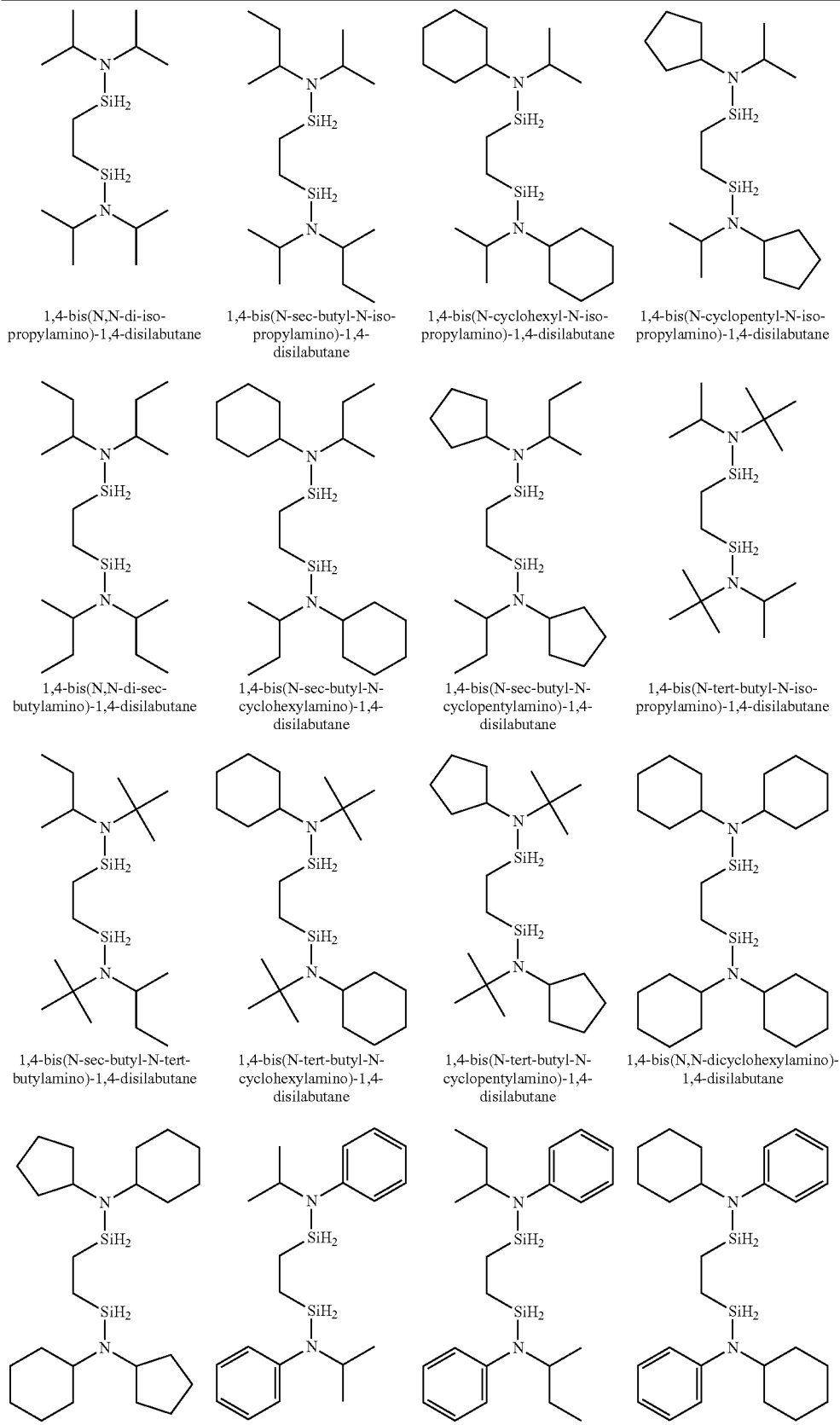

TABLE 6-continued

Exemplary Organoaminocarbosilane (more specifically 1,4-bis(organoamino)-1,4-disilabutane) Compounds

| 1,4-bis(N-cyclohexyl-N-cyclopentylamino)-1,4-disilabutane | 1,4-bis(N-phenyl-N-iso-propylamino)-1,4-disilabutane | 1,4-bis(N-sec-butyl-N-phenylamino)-1,4-disilabutane | 1,4-bis(N-cyclohexyl-N-phenylamino)-1,4-disilabutane |
|---|---|---|---|
| 1,4-bis(N-cyclopentyl-N-phenylamino)-1,4-disilabutane | 1,4-bis(N-ethyl-N-phenylamino)-1,4-disilabutane | 1,4-bis(N,N-dimethylamino)-1,4-disilabutane | 1,4-bis(N,N-diethylamino)-1,4-disilabutane |
| 1,4-bis(N,N-di-n-propylamino)-1,4-disilabutane | | | |

TABLE 7

Exemplary Organoaminocarbosilane (more specifically organoamino-1,3-disilapropane) Compounds

| 1-(N-methyl-N-iso-propylamino)-1,3-disilapropane | 1-(N-sec-butyl-N-methylamino)-1,3-disilapropane | 1-(N-cyclohexyl-N-methylamino)-1,3-disilapropane | 1-(N-methyl-N-cyclopentylamino)-1,3-disilapropane |
|---|---|---|---|
| 1-(N-ethyl-N-iso-propylamino)-1,3-disilapropane | 1-(N-sec-butyl-N-ethylamino)-1,3-disilapropane | 1-(N-ethyl-N-cyclohexylamino)-1,3-disilapropane | 1-(N-ethyl-N-cyclopentylamino)-1,3-disilapropane |

TABLE 7-continued

Exemplary Organoaminocarbosilane (more specifically organoamino-1,3-disilapropane) Compounds

| 1-(N-n-propyl-N-iso-propylamino)-1,3-disilapropane | 1-(N-sec-butyl-N-n-propylamino)-1,3-disilapropane | 1-(N-cyclohexyl-N-n-propylamino)-1,3-disilapropane | 1-(N-cyclopentyl-N-n-propylamino)-1,3-disilapropane |
| --- | --- | --- | --- |
| 1-(N,N-di-iso-propylamino)-1,3-disilapropane | 1-(N-sec-butyl-N-iso-propylamino)-1,3-disilapropane | 1-(N-cyclohexyl-N-iso-propylamino)-1,3-disilapropane | 1-(N-cyclopentyl-N-iso-propylamino)-1,3-disilapropane |
| 1-(N,N-di-sec-butylamino)-1,3-disilapropane | 1-(N-sec-butyl-N-cyclohexylamino)-1,3-disilapropane | 1-(N-sec-butyl-N-cyclopentylamino)-1,3-disilapropane | 1-(N-tert-butyl-N-isopropylamino)-1,3-disilapropane |
| 1-(N-sec-butyl-N-tertbutylamino)-1,3-disilapropane | 1-(N-tert-butyl-N-cyclohexylamino)-1,3-disilapropane | 1-(N-tert-butyl-N-cyclopentylamino)-1,3-disilapropane | 1-(N,N-dicyclohexylamino)-1,3-disilapropane |
| 1-(N-cyclohexyl-N-cyclopentylamino)-1,3-disilapropane | 1-(N-phenyl-N-iso-propylamino)-1,3-disilapropane | 1-(N-sec-butyl-N-phenylamino)-1,3-disilapropane | 1-(N-cyclohexyl-N-phenylamino)-1,3-disilapropane |

TABLE 7-continued

Exemplary Organoaminocarbosilane (more specifically organoamino-1,3-disilapropane) Compounds

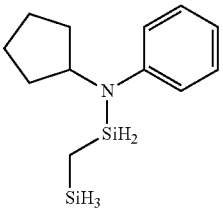
1-(N-cyclopentyl-N-phenylamino)-1,3-disilapropane

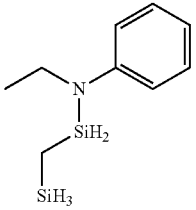
1-(N-ethyl-N-phenylamino)-1,3-disilapropane

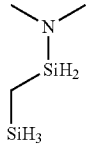
1-(N,N-dimethylamino)-1,3-disilapropane

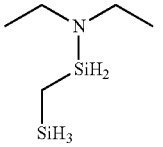
1-(N,N-dimethylamino)-1,3-disilapropane

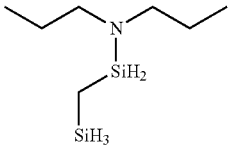
1-(N,N-di-n-propylamino)-1,3-disilapropane

TABLE 8

Exemplary Organoaminocarbosilane (more specifically 1,3-bis(organoamino)-1,3-disilapropane) Compounds

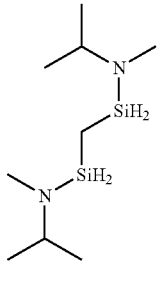
1,3-bis(N-methyl-N-iso-propylamino)-1,3-disilapropane

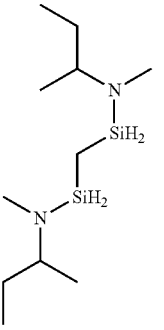
1,3-bis(N-sec-butyl-N-methylamino)-1,3-disilapropane

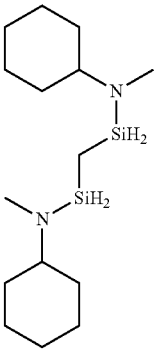
1,3-bis(N-cyclohexyl-N-methylamino)-1,3-disilapropane

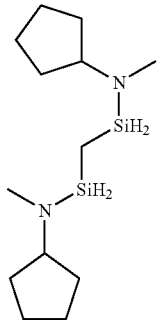
1,3-bis(N-methyl-N-cyclopentylamino)-1,3-disilapropane

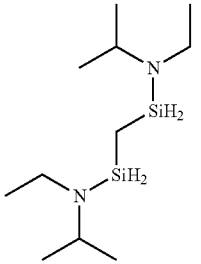
1,3-bis(N-ethyl-N-iso-propylamino)-1,3-disilapropane

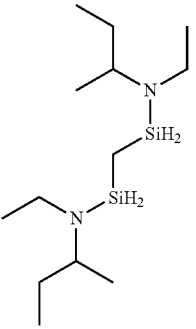
1,3-bis(N-sec-butyl-N-ethylamino)-1,3-disilapropane

TABLE 8-continued

Exemplary Organoaminocarbosilane (more specifically 1,3-bis(organoamino)-1,3-disilapropane) Compounds

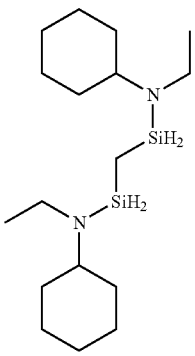

1,3-bis(N-ethyl-N-cyclohexylamino)-1,3-disilapropane

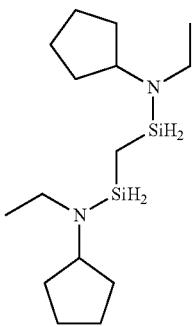

1,3-bis(N-ethyl-N-cyclopentylamino)-1,3-disilapropane

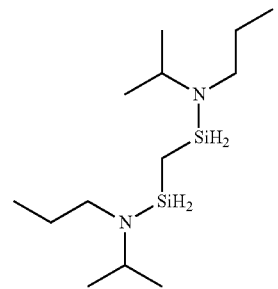

1,3-bis(N-n-propyl-N-iso-propylamino)-1,3-disilapropane

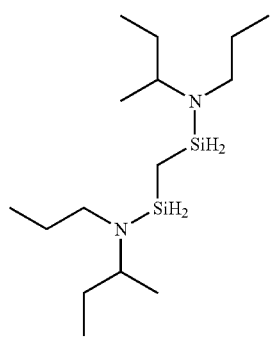

1,3-bis(N-sec-butyl-N-n-propylamino)-1,3-disilapropane

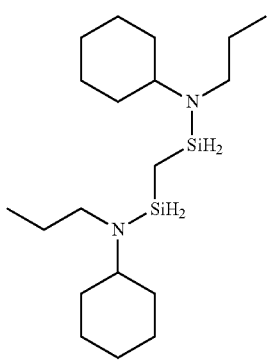

1,3-bis(N-cyclohexyl-N-n-propylamino)-1,3-disilapropane

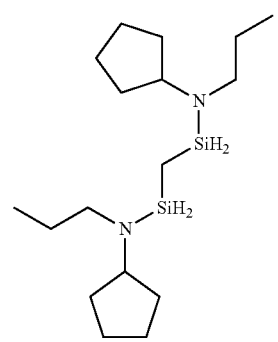

1,3-bis(N-cyclopentyl-N-n-propylamino)-1,3-disilapropane

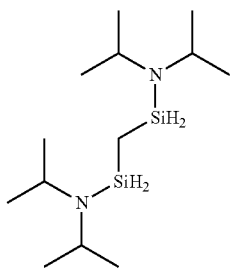

1,3-bis(N,N-di-iso-propylamino)-1,3-disilapropane

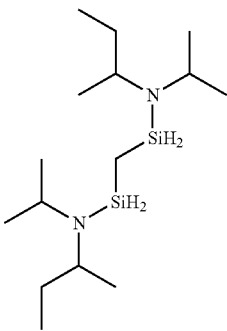

1,3-bis(N-sec-butyl-N-iso-propylamino)-1,3-disilapropane

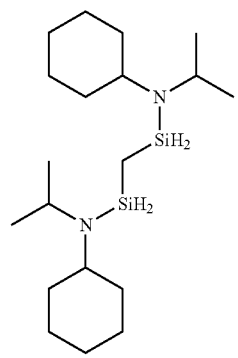

1,3-bis(N-cyclohexyl-N-iso-propylamino)-1,3-disilapropane

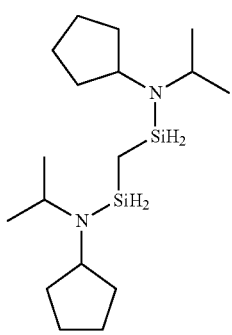

1,3-bis(N-cyclopentyl-N-iso-propylamino)-1,3-disilapropane

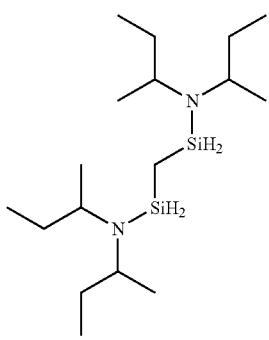

1,3-bis(N,N-di-sec-butylamino)-1,3-disilapropane

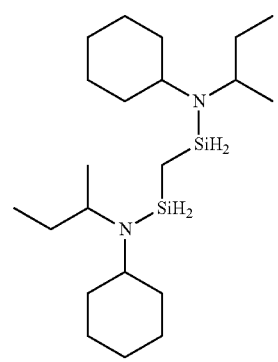

1,3-bis(N-sec-butyl-N-cyclohexylamino)-1,3-disilapropane

TABLE 8-continued

Exemplary Organoaminocarbosilane (more specifically 1,3-bis(organoamino)-1,3-disilapropane) Compounds

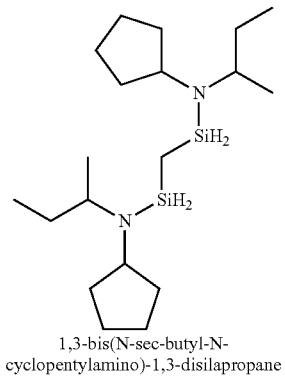

1,3-bis(N-sec-butyl-N-cyclopentylamino)-1,3-disilapropane

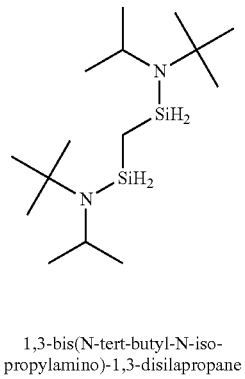

1,3-bis(N-tert-butyl-N-iso-propylamino)-1,3-disilapropane

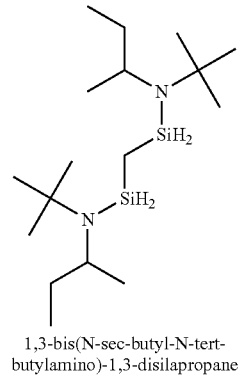

1,3-bis(N-sec-butyl-N-tert-butylamino)-1,3-disilapropane

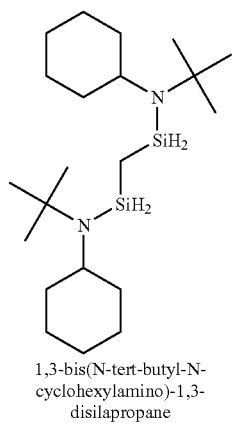

1,3-bis(N-tert-butyl-N-cyclohexylamino)-1,3-disilapropane

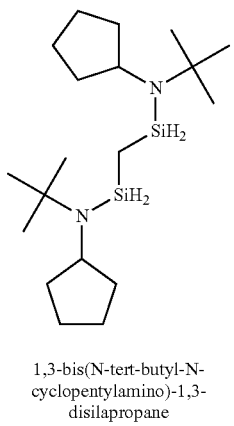

1,3-bis(N-tert-butyl-N-cyclopentylamino)-1,3-disilapropane

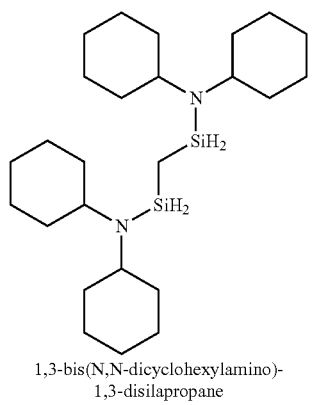

1,3-bis(N,N-dicyclohexylamino)-1,3-disilapropane

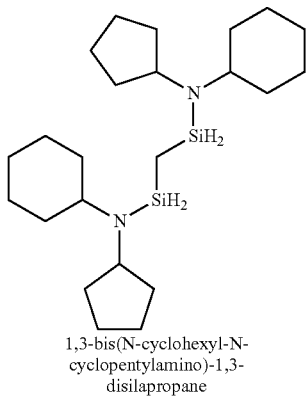

1,3-bis(N-cyclohexyl-N-cyclopentylamino)-1,3-disilapropane

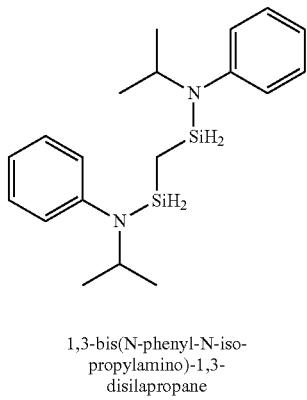

1,3-bis(N-phenyl-N-iso-propylamino)-1,3-disilapropane

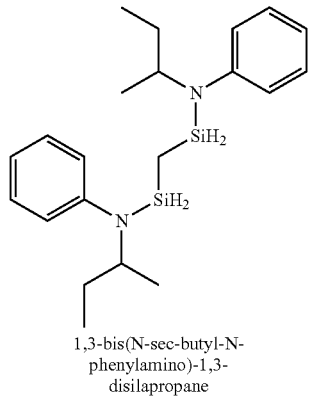

1,3-bis(N-sec-butyl-N-phenylamino)-1,3-disilapropane

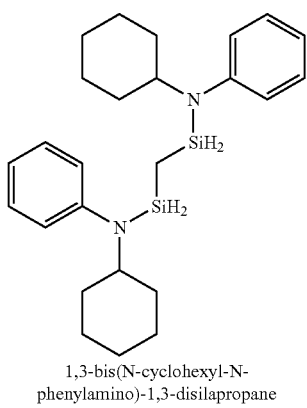

1,3-bis(N-cyclohexyl-N-phenylamino)-1,3-disilapropane

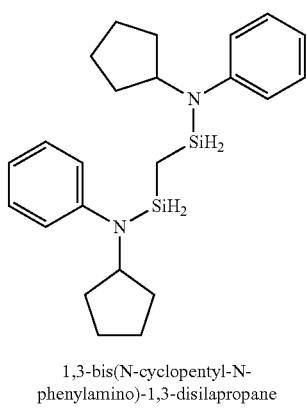

1,3-bis(N-cyclopentyl-N-phenylamino)-1,3-disilapropane

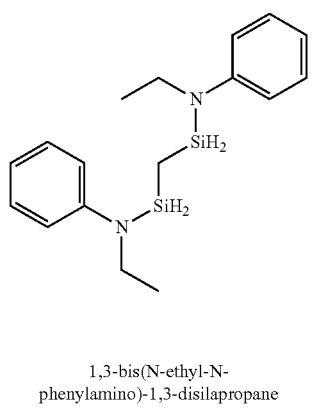

1,3-bis(N-ethyl-N-phenylamino)-1,3-disilapropane

TABLE 8-continued

Exemplary Organoaminocarbosilane (more specifically 1,3-bis(organoamino)-1,3-disilapropane) Compounds 1,3-bis(N,N-dimethylamino)-1,3-disilapropane 1,3-bis(N,N-diethylamino)-1,3-disilapropane 1,3-bis(N,N-di-n-propylamino)-1,3-disilapropane

TABLE 9

Exemplary Organoaminocarbosilane (more specifically 1-organoamino-2-methyl-1,3-disilapropane) Compounds 1-(N-methyl-N-iso-propylamino)-2-methyl-1,3-disilapropane 1-(N-sec-butyl-N-methylamino)-2-methyl-1,3-disilapropane 1-(N-cyclohexyl-N-methylamino)-2-methyl-1,3-disilapropane 1-(N-methyl-N-cyclopentylamino)-2-methyl-1,3-disilapropane 1-(N-ethyl-N-iso-propylamino)-2-methyl-1,3-disilapropane 1-(N-sec-butyl-N-ethylamino)-2-methyl-1,3-disilapropane 1-(N-ethyl-N-cyclohexylamino)-2-methyl-1,3-disilapropane 1-(N-ethyl-N-cyclopentylamino)-2-methyl-1,3-disilapropane 1-(N-n-propyl-N-iso-propylamino)-2-methyl-1,3-disilapropane 1-(N-sec-butyl-N-n-propylamino)-2-methyl-1,3-disilapropane 1-(N-cyclohexyl-N-n-propylamino)-2-methyl-1,3-disilapropane 1-(N-cyclopentyl-N-n-propylamino)-2-methyl-1,3-disilapropane TABLE 9-continued Exemplary Organoaminocarbosilane (more specifically 1-organoamino-2-methyl-1,3-disilapropane) Compounds

| 1-(N,N-di-iso-propylamino)-2-methyl-1,3-disilapropane | 1-(N-sec-butyl-N-iso-propylamino)-2-methyl-1,3-disilapropane | 1-(N-cyclohexyl-N-iso-propylamino)-2-methyl-1,3-disilapropane | 1-(N-cyclopentyl-N-iso-propylamino)-2-methyl-1,3-disilapropane |
| --- | --- | --- | --- |
| 1-(N,N-di-sec-butylamino)-2-methyl-1,3-disilapropane | 1-(N-sec-butyl-N-cyclohexylamino)-2-methyl-1,3-disilapropane | 1-(N-sec-butyl-N-cyclopentylamino)-2-methyl-1,3-disilapropane | 1-(N-tert-butyl-N-iso-propylamino)-2-methyl-1,3-disilapropane |
| 1-(N-sec-butyl-N-tert-butylamino)-2-methyl-1,3-disilapropane | 1-(N-tert-butyl-N-cyclohexylamino)-2-methyl-1,3-disilapropane | 1-(N-tert-butyl-N-cyclopentylamino)-2-methyl-1,3-disilapropane | 1-(N,N-dicyclohexylamino)-2-methyl-1,3-disilapropane |
| 1-(N-cyclohexyl-N-cyclopentylamino)-2-methyl-1,3-disilapropane | 1-(N-phenyl-N-iso-propylamino)-2-methyl-1,3-disilapropane | 1-(N-sec-butyl-N-phenylamino)-2-methyl-1,3-disilapropane | 1-(N-cyclohexyl-N-phenylamino)-2-methyl-1,3-disilapropane |
| 1-(N-cyclopentyl-N-phenylamino)-2-methyl-1,3-disilapropane | 1-(N-ethyl-N-phenylamino)-2-methyl-1,3-disilapropane | 1-(N,N-dimethylamino)-2-methyl-1,3-disilapropane | 1-(N,N-dimethylamino)-2-methyl-1,3-disilapropane |
| 1-(N,N-di-n-propylamino)-2-methyl-1,3-disilapropane | | | |

TABLE 10
Exemplary Organoaminocarbosilane (more specifically 1,3-bis(organoamino)-2-methyl-1,3-disilapropane) Compounds
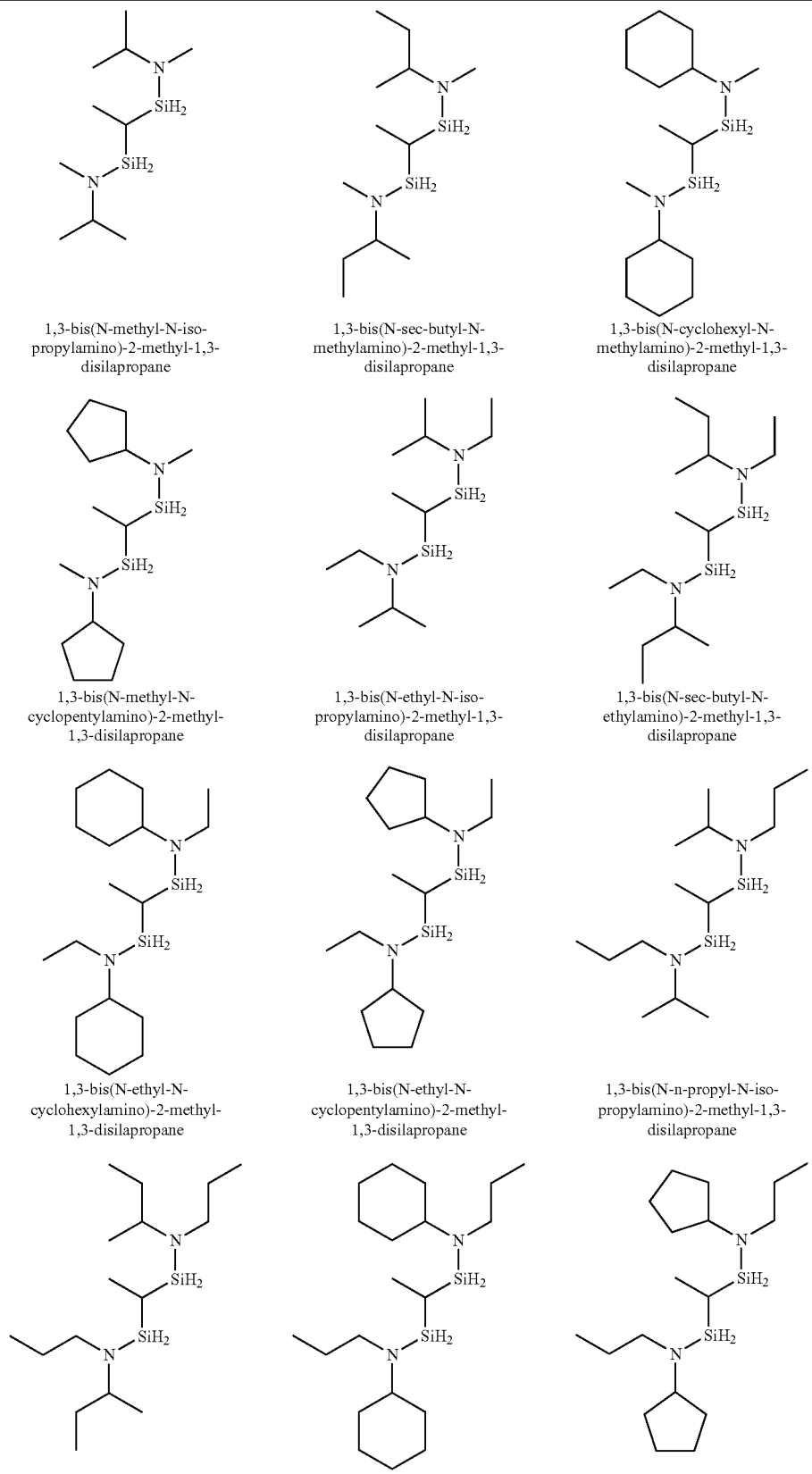

TABLE 10-continued

Exemplary Organoaminocarbosilane (more specifically 1,3-bis(organoamino)-
2-methyl-1,3-disilapropane) Compounds

| 1,3-bis(N-sec-butyl-N-n-propylamino)-2-methyl-1,3-disilapropane | 1,3-bis(N-cyclohexyl-N-n-propylamino)-2-methyl-1,3-disilapropane | 1,3-bis(N-cyclopentyl-N-n-propylamino)-2-methyl-1,3-disilapropane |

| 1,3-bis(N,N-di-iso-propylamino)-2-methyl-1,3-disilapropane | 1,3-bis(N-sec-butyl-N-iso-propylamino)-2-methyl-1,3-disilapropane | 1,3-bis(N-cyclohexyl-N-iso-propylamino)-2-methyl-1,3-disilapropane |

| 1,3-bis(N-cyclopentyl-N-iso-propylamino)-2-methyl-1,3-disilapropane | 1,3-bis(N,N-di-sec-butylamino)-2-methyl-1,3-disilapropane | 1,3-bis(N-sec-butyl-N-cyclohexylamino)-2-methyl-1,3-disilapropane |

| 1,3-bis(N-sec-butyl-N-cyclopentylamino)-2-methyl-1,3-disilapropane | 1,3-bis(N-tert-butyl-N-iso-propylamino)-2-methyl-1,3-disilapropane | 1,3-bis(N-sec-butyl-N-tert-butylamino)-2-methyl-1,3-disilapropane |

TABLE 10-continued

Exemplary Organoaminocarbosilane (more specifically 1,3-bis(organoamino)-2-methyl-1,3-disilapropane) Compounds

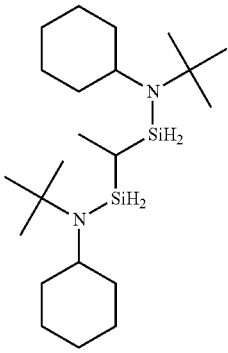

1,3-bis(N-tert-butyl-N-cyclohexylamino)-2-methyl-1,3-disilapropane

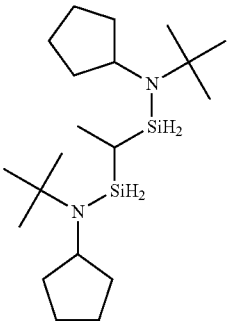

1,3-bis(N-tert-butyl-N-cyclopentylamino)-2-methyl-1,3-disilapropane

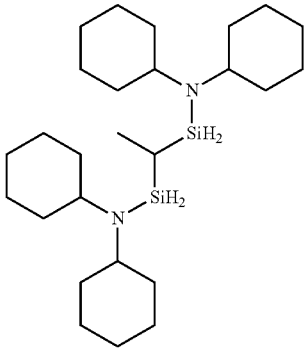

1,3-bis(N,N-dicyclohexylamino)-2-methyl-1,3-disilapropane

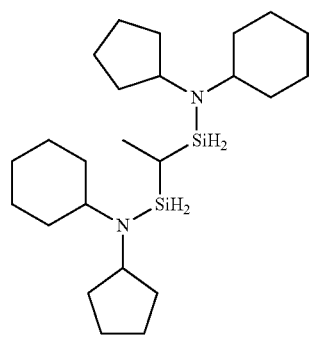

1,3-bis(N-cyclohexyl-N-cyclopentylamino)-2-methyl-1,3-disilapropane

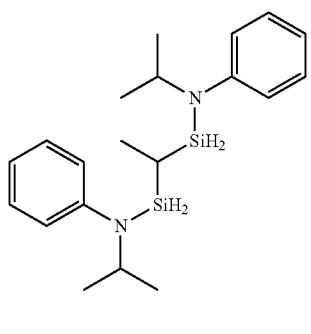

1,3-bis(N-phenyl-N-iso-propylamino)-2-methyl-1,3-disilapropane

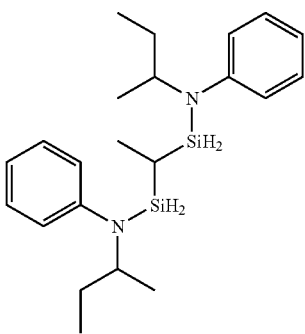

1,3-bis(N-sec-butyl-N-phenylamino)-2-methyl-1,3-disilapropane

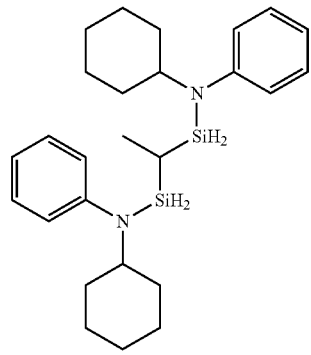

1,3-bis(N-cyclohexyl-N-phenylamino)-2-methyl-1,3-disilapropane

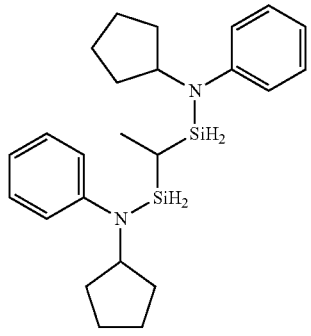

1,3-bis(N-cyclopentyl-N-phenylamino)-2-methyl-1,3-disilapropane

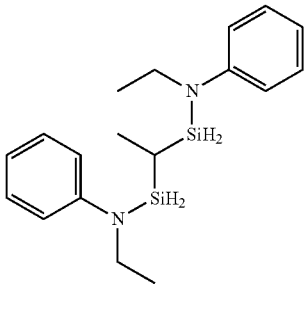

1,3-bis(N-ethyl-N-phenylamino)-2-methyl-1,3-disilapropane

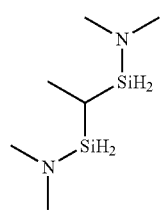

1,3-bis(N,N-dimethylamino)-2-methyl-1,3-disilapropane

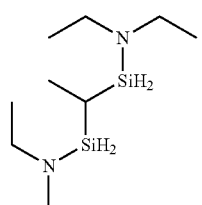

1,3-bis(N,N-diethylamino)-2-methyl-1,3-disilapropane

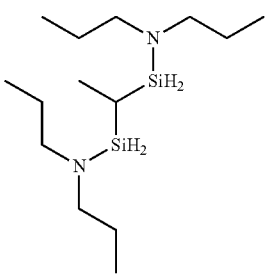

1,3-bis(N,N-di-n-propylamino)-2-methyl-1,3-disilapropane

TABLE 11

Exemplary Organoaminocarbosilane (more specifically organoamino-silacyclopentane) Compounds

| | | | |
|---|---|---|---|
| 1-(N-methyl-N-iso-propylamino)-silacyclopentane | 1-(N-sec-butyl-N-methylamino)-silacyclopentane | 1-(N-cyclohexyl-N-methylamino)-silacyclopentane | 1-(N-methyl-N-cyclopentylamino)-silacyclopentane |
| 1-(N-ethyl-N-iso-propylamino)-silacyclopentane | 1-(N-sec-butyl-N-ethylamino)-silacyclopentane | 1-(N-ethyl-N-cyclohexylamino)-silacyclopentane | 1-(N-ethyl-N-cyclopentylamino)-silacyclopentane |
| 1-(N-n-propy-N-iso-propylamino)-silacyclopentane | 1-(N-sec-butyl-N-n-propylamino)-silacyclopentane | 1-(N-cyclohexyl-N-n-propylamino)-silacyclopentane | 1-(N-cyclopentyl-N-n-propylamino)-silacyclopentane |
| 1-(N,N-di-iso-propylamino)-silacyclopentane | 1-(N-sec-butyl-N-iso-propylamino)-silacyclopentane | 1-(N-cyclohexyl-N-iso-propylamino)-silacyclopentane | 1-(N-cyclopentyl-N-iso-propylamino)-silacyclopentane |
| 1-(N,N-di-sec-butylamino)-silacyclopentane | 1-(N-sec-butyl-N-cyclohexylamino)-silacyclopentane | 1-(N-sec-butyl-N-cyclopentylamino)-silacyclopentane | 1-(N-tert-butyl-N-iso-propylamino)-silacyclopentane |

TABLE 11-continued

Exemplary Organoaminocarbosilane (more specifically organoamino-silacyclopentane) Compounds

| 1-(N-sec-butyl-N-tert-butylamino)-silacyclopentane | 1-(N-tert-butyl-N-cyclohexylamino)-silacyclopentane | 1-(N-tert-butyl-N-cyclopentylamino)-silacyclopentane | 1-(N,N-dicyclohexylamino)-silacyclopentane |
|---|---|---|---|
| 1-(N-cyclohexyl-N-cyclopentylamino)-silacyclopentane | 1-(N-phenyl-N-iso-propylamino)-silacyclopentane | 1-(N-sec-butyl-N-phenylamino)-silacyclopentane | 1-(N-cyclohexyl-N-phenylamino)-silacyclopentane |
| 1-(N-cyclopentyl-N-phenylamino)-silacyclopentane | 1-(N-ethyl-N-phenylamino)-silacyclopentane | 1-(N,N-diethylamino)-silacyclopentane | 1-(N,N-diethylamino)-silacyclopentane |
| 1-(N,N-di-n-propylamino)-silacyclopentane | | | |

TABLE 12

Exemplary Organoaminocarbosilane (more specifically organoamino-methylsilacyclopentane) Compounds

| 1-(N-methyl-N-iso-propylamino)-1-methyl-silacyclopentane | 1-(N-sec-butyl-N-methylamino)-1-methyl-silacyclopentane | 1-(N-cyclohexyl-N-methylamino)-1-methyl-silacyclopentane | 1-(N-methyl-N-cyclopentylamino)-1-methyl-silacyclopentane |
|---|---|---|---|

TABLE 12-continued
Exemplary Organoaminocarbosilane (more specifically organoamino-methylsilacyclopentane) Compounds
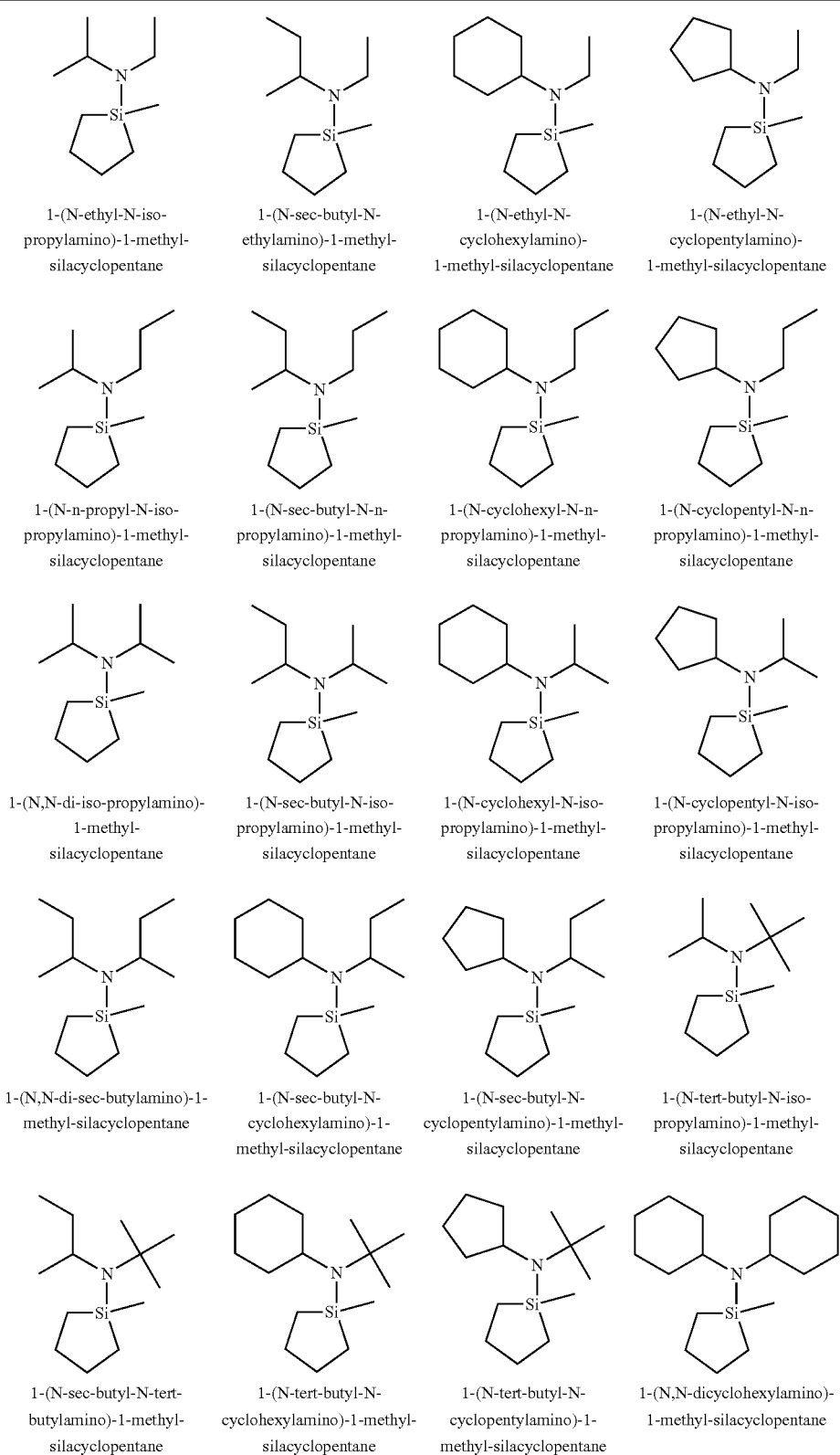

TABLE 12-continued

Exemplary Organoaminocarbosilane (more specifically organoamino-methylsilacyclopentane) Compounds

| 1-(N-cyclohexyl-N-cyclopentylamino)-1-methyl-silacyclopentane | 1-(N-phenyl-N-iso-propylamino)-1-methyl-silacyclopentane | 1-(N-sec-butyl-N-phenylamino)-1-methyl-silacyclopentane | 1-(N-cyclohexyl-N-phenylamino)-1-methyl-silacyclopentane |
|---|---|---|---|
| 1-(N-cyclopentyl-N-phenylamino)-1-methyl-silacyclopentane | 1-(N-ethyl-N-phenylamino)-1-methyl-silacyclopentane | 1-(N,N-dimethylamino)-1-methyl-silacyclopentane | 1-(N,N-dimethylamino)-1-methyl-silacyclopentane |
| 1-(N,N-di-n-propylamino)-1-methyl-silacyclopentane | | | |

TABLE 13

Exemplary Organoaminocarbosilane (more specifically organoamino-silacyclobutane having cyclic four-membered ring) Compounds

| 1-(N-methyl-N-iso-propylamino)-silacyclobutane | 1-(N-sec-butyl-N-methylamino)-silacyclobutane | 1-(N-cyclohexyl-N-methylamino)-silacyclobutane | 1-(N-methyl-N-cyclopentylamino)-silacyclobutane |
|---|---|---|---|
| 1-(N-ethyl-N-iso-propylamino)-silacyclobutane | 1-(N-sec-butyl-N-ethylamino)-silacyclobutane | 1-(N-ethyl-N-cyclohexylamino)-silacyclobutane | 1-(N-ethyl-N-cyclopentylamino)-silacyclobutane |

TABLE 13-continued
Exemplary Organoaminocarbosilane (more specifically organoamino-
silacyclobutane having cyclic four-membered ring) Compounds
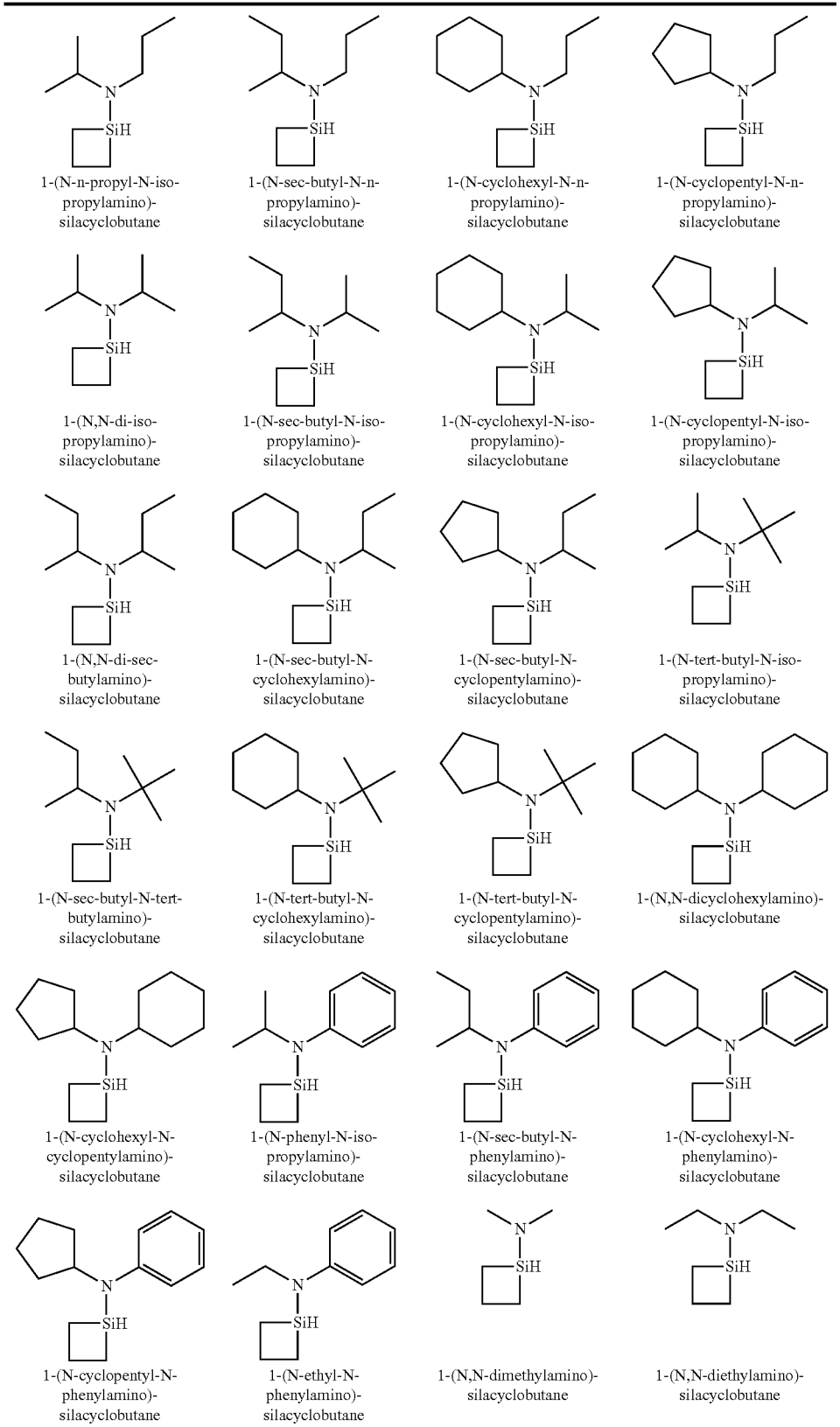

TABLE 13-continued

Exemplary Organoaminocarbosilane (more specifically organoamino-silacyclobutane having cyclic four-membered ring) Compounds

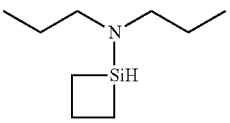

1-(N,N-di-n-propylamino)-silacyclobutane

TABLE 14

Exemplary Organoaminocarbosilane (more specifically organoamino-1,3-disilacyclobutane having cyclic four-membered ring) Compounds

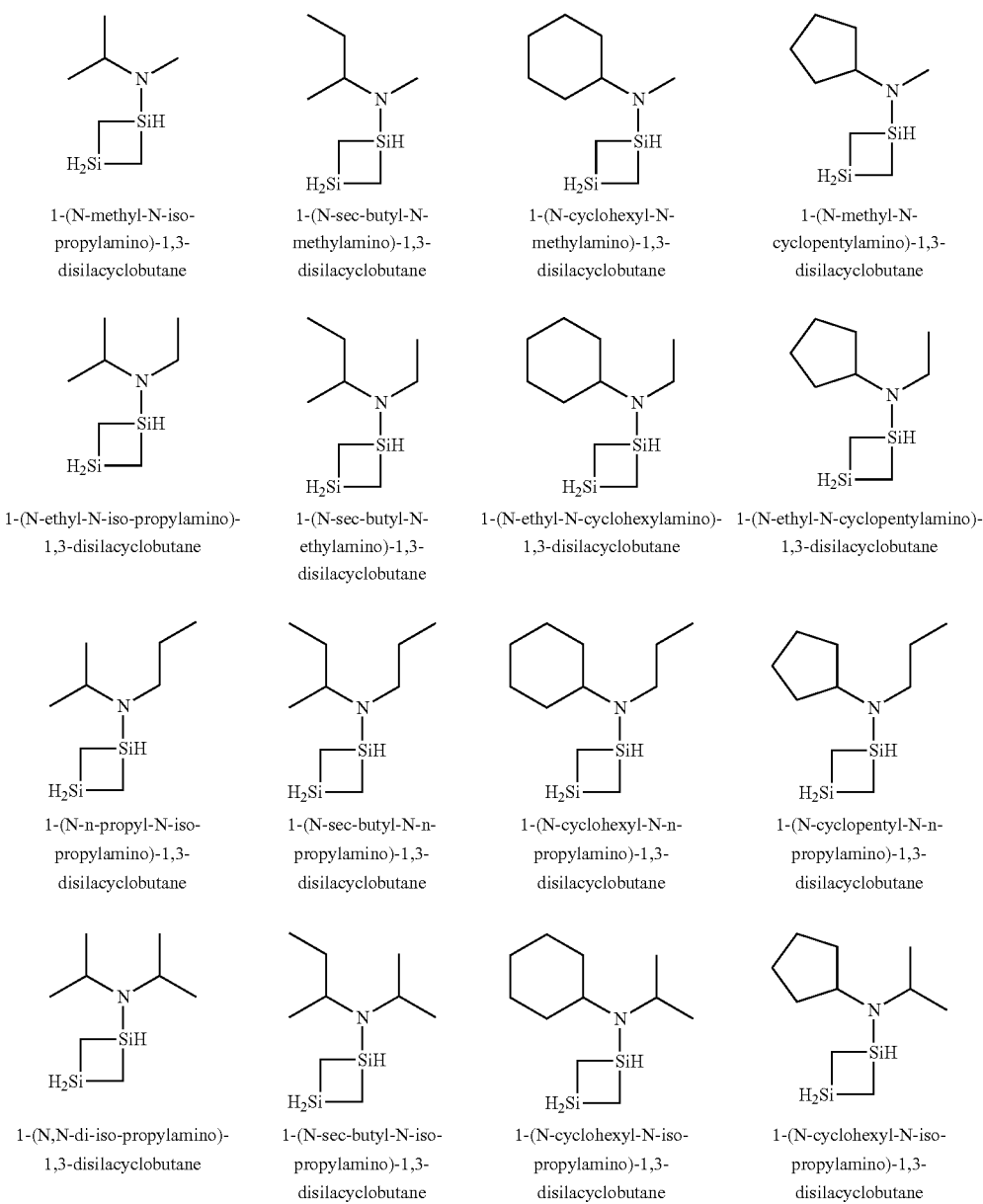

| 1-(N-methyl-N-iso-propylamino)-1,3-disilacyclobutane | 1-(N-sec-butyl-N-methylamino)-1,3-disilacyclobutane | 1-(N-cyclohexyl-N-methylamino)-1,3-disilacyclobutane | 1-(N-methyl-N-cyclopentylamino)-1,3-disilacyclobutane |
| 1-(N-ethyl-N-iso-propylamino)-1,3-disilacyclobutane | 1-(N-sec-butyl-N-ethylamino)-1,3-disilacyclobutane | 1-(N-ethyl-N-cyclohexylamino)-1,3-disilacyclobutane | 1-(N-ethyl-N-cyclopentylamino)-1,3-disilacyclobutane |
| 1-(N-n-propyl-N-iso-propylamino)-1,3-disilacyclobutane | 1-(N-sec-butyl-N-n-propylamino)-1,3-disilacyclobutane | 1-(N-cyclohexyl-N-n-propylamino)-1,3-disilacyclobutane | 1-(N-cyclopentyl-N-n-propylamino)-1,3-disilacyclobutane |
| 1-(N,N-di-iso-propylamino)-1,3-disilacyclobutane | 1-(N-sec-butyl-N-iso-propylamino)-1,3-disilacyclobutane | 1-(N-cyclohexyl-N-iso-propylamino)-1,3-disilacyclobutane | 1-(N-cyclohexyl-N-iso-propylamino)-1,3-disilacyclobutane |

TABLE 14-continued

Exemplary Organoaminocarbosilane (more specifically organoamino-1,3-disilacyclobutane having cyclic four-membered ring) Compounds

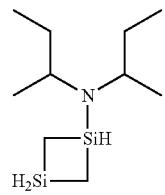
1-(N,N-di-sec-butylamino)-1,3-disilacyclobutane

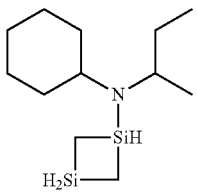
1-(N-sec-butyl-N-cyclohexylamino)-1,3-disilacyclobutane

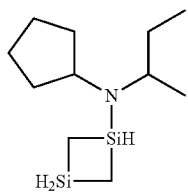
1-(N-sec-butyl-N-cyclopentylamino)-1,3-disilacyclobutane

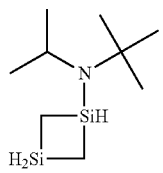
1-(N-tert-butyl-N-iso-propylamino)-1,3-disilacyclobutane

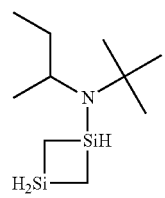
1-(N-sec-butyl-N-tert-butylamino)-1,3-disilacyclobutane

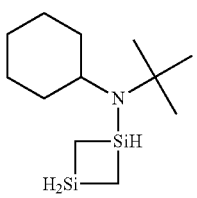
1-(N-tert-butyl-N-cyclohexylamino)-1,3-disilacyclobutane

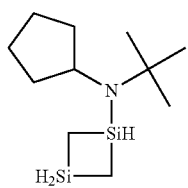
1-(N-tert-butyl-N-cyclopentylamino)-1,3-disilacyclobutane

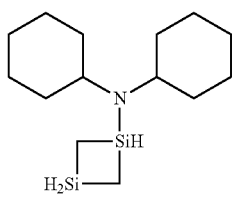
1-(N,N-dicylclohexylamino)-1,3-disilacyclobutane

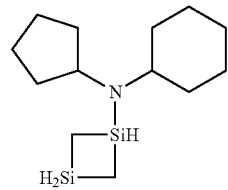
1-(N-cyclohexyl-N-cyclopentylamino)-1,3-disilacyclobutane

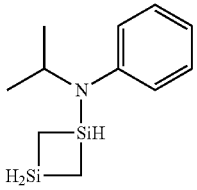
1-(N-phenyl-N-iso-propylamino)-1,3-disilacyclobutane

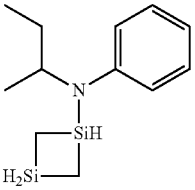
1-(N-sec-butyl-N-phenylamino)-1,3-disilacyclobutane

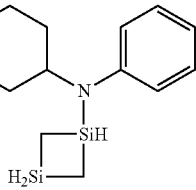
1-(N-cyclohexyl-N-phenylamino)-1,3-disilacyclobutane

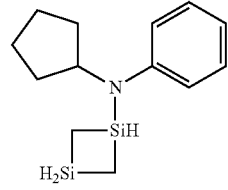
1-(N-cyclopentyl-N-phenylamino)-1,3-disilacyclobutane

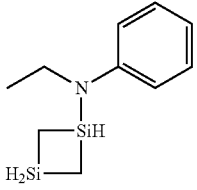
1-(N-ethyl-N-phenylamino)-1,3-disilacyclobutane

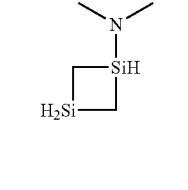
1-(N,N-dimethylamino)-1,3-disilacyclobutane

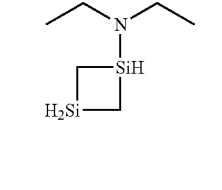
1-(N,N-diethylamino)-1,3-disilacyclobutane

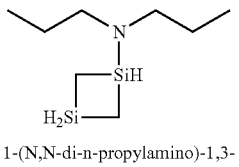
1-(N,N-di-n-propylamino)-1,3-disilacyclobutane

TABLE 15

Exemplary Organoaminocarbosilane (more specifically 1,3-bis(organoamino)-1,3-disilacyclobutane having cyclic four-membered ring) Compounds

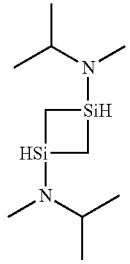
1,3-bis(N-methyl-N-iso-propylamino)-1,3-disilacyclobutane

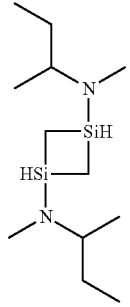
1,3-bis(N-sec-butyl-N-methylamino)-1,3-disilacyclobutane

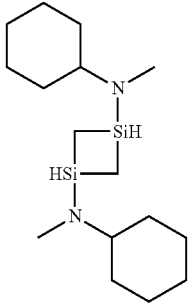
1,3-bis(N-cyclohexyl-N-methylamino)-1,3-disilacyclobutane

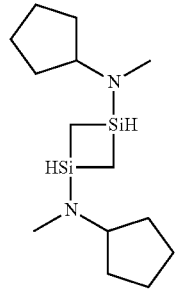
1,3-bis(N-methyl-N-cyclopentylamino)-1,3-disilacyclobutane

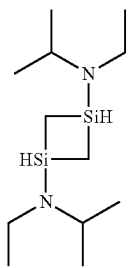
1,3-bis(N-ethyl-N-iso-propylamino)-1,3-disilacyclobutane

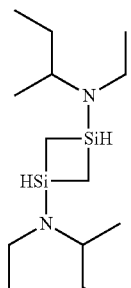
1,3-bis(N-sec-butyl-N-ethylamino)-1,3-disilacyclobutane

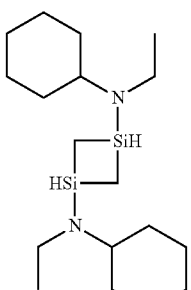
1,3-bis(N-ethyl-N-cyclohexylamino)-1,3-disilacyclobutane

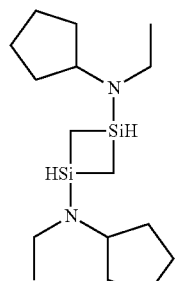
1,3-bis(N-ethyl-N-cyclopentylamino)-1,3-disilacyclobutane

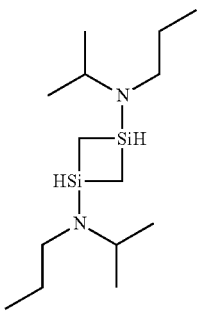
1,3-bis(N-n-propyl-N-iso-propylamino)-1,3-disilacyclobutane

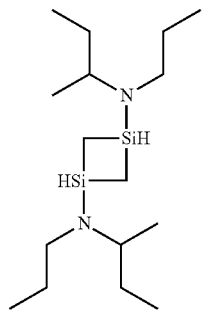
1,3-bis(N-sec-butyl-N-n-propylamino)-1,3-disilacyclobutane

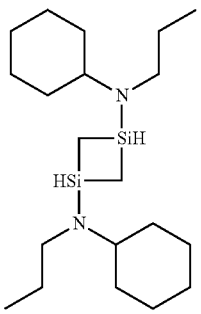
1,3-bis(N-cyclohexyl-N-n-propylamino)-1,3-disilacyclobutane

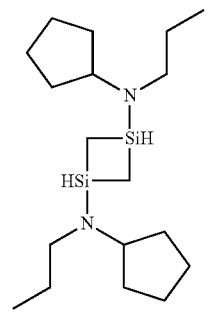
1,3-bis(N-cyclopentyl-N-n-propylamino)-1,3-disilacyclobutane

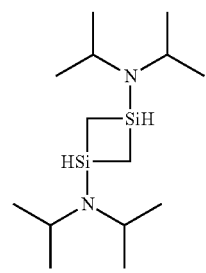
1,3-bis(N,N-di-iso-propylamino)-1,3-disilacyclobutane

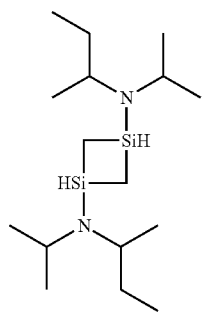
1,3-bis(N-sec-butyl-N-iso-propylamino)-1,3-disilacyclobutane

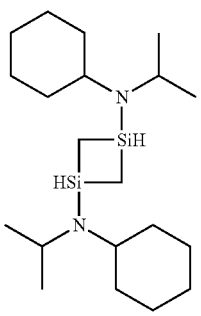
1,3-bis(N-cyclohexyl-N-iso-propylamino)-1,3-disilacyclobutane

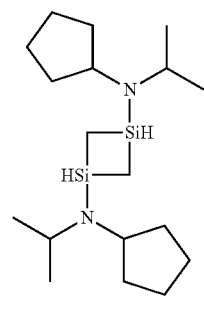
1,3-bis(N-cyclopentyl-N-iso-propylamino)-1,3-disilacyclobutane

TABLE 15-continued
Exemplary Organoaminocarbosilane (more specifically 1,3-bis(organoamino)-1,3-disilacyclobutane having cyclic four-membered ring) Compounds
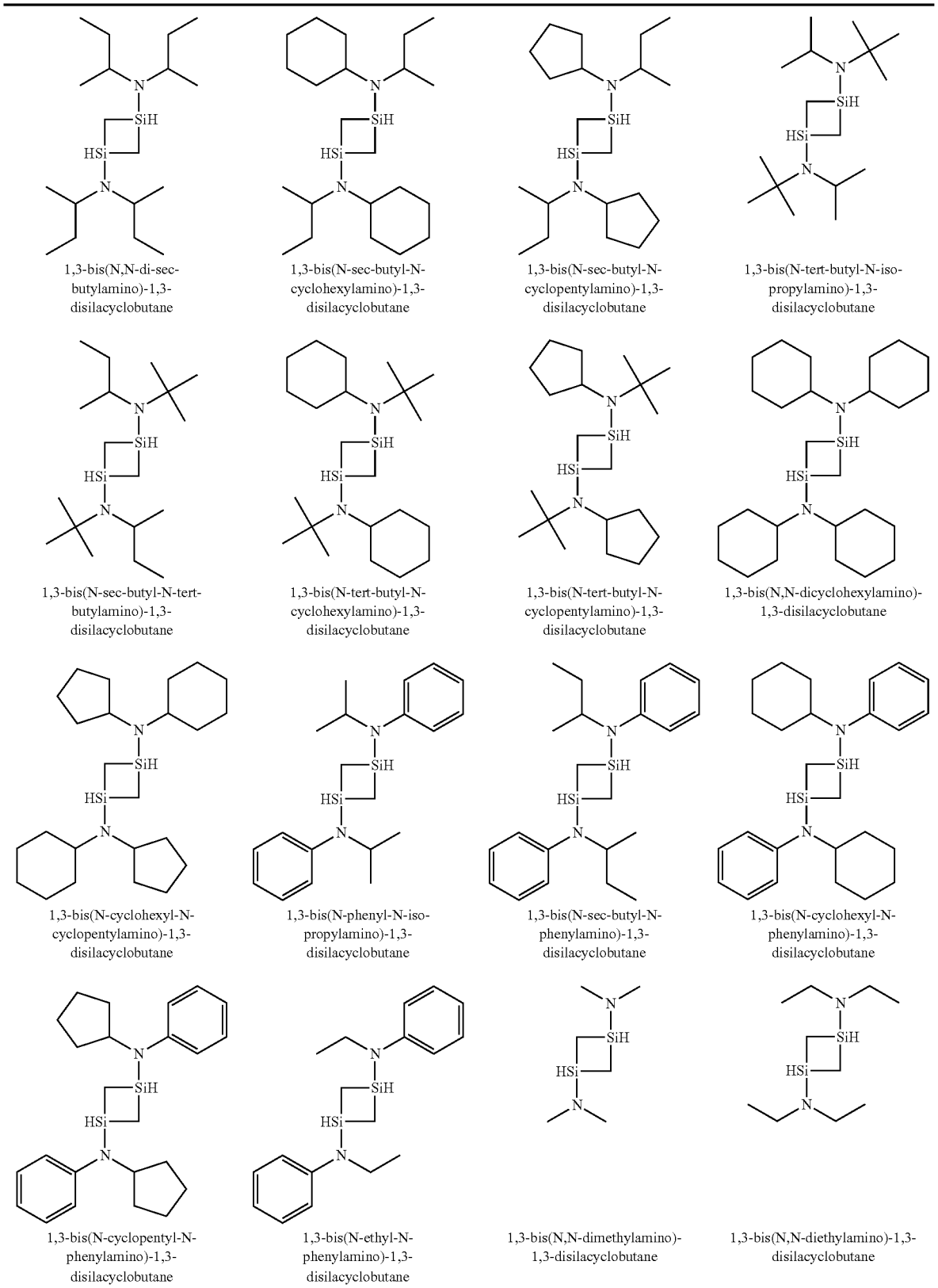

TABLE 15-continued

Exemplary Organoaminocarbosilane (more specifically 1,3-bis(organoamino)-
1,3-disilacyclobutane having cyclic four-membered ring) Compounds

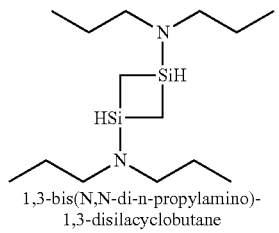

1,3-bis(N,N-di-n-propylamino)-
1,3-disilacyclobutane

TABLE 16

Exemplary Organoaminocarbosilane (more specifically organoaminomethylsilane) Compounds

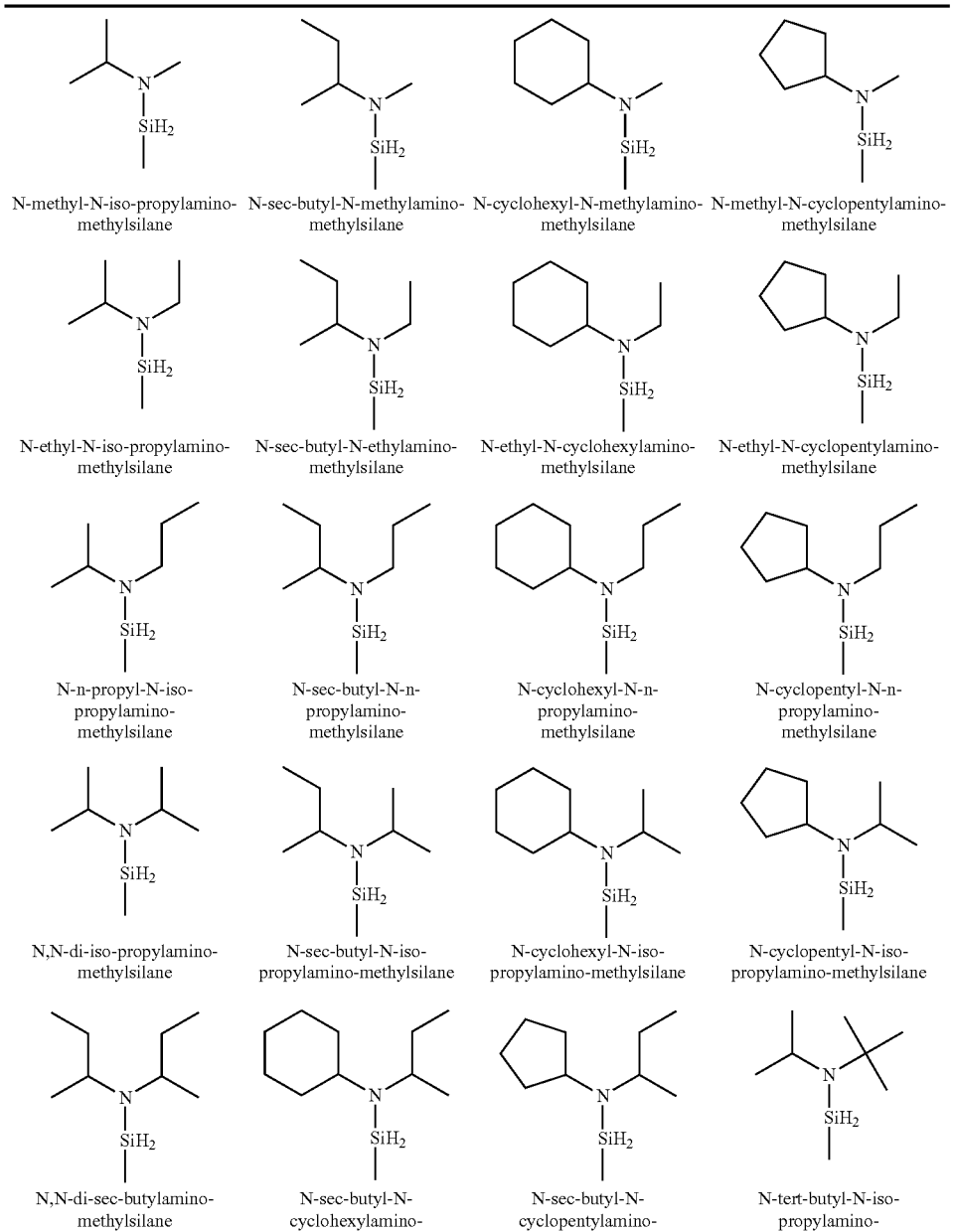

| N-methyl-N-iso-propylamino-methylsilane | N-sec-butyl-N-methylamino-methylsilane | N-cyclohexyl-N-methylamino-methylsilane | N-methyl-N-cyclopentylamino-methylsilane |
| N-ethyl-N-iso-propylamino-methylsilane | N-sec-butyl-N-ethylamino-methylsilane | N-ethyl-N-cyclohexylamino-methylsilane | N-ethyl-N-cyclopentylamino-methylsilane |
| N-n-propyl-N-iso-propylamino-methylsilane | N-sec-butyl-N-n-propylamino-methylsilane | N-cyclohexyl-N-n-propylamino-methylsilane | N-cyclopentyl-N-n-propylamino-methylsilane |
| N,N-di-iso-propylamino-methylsilane | N-sec-butyl-N-iso-propylamino-methylsilane | N-cyclohexyl-N-iso-propylamino-methylsilane | N-cyclopentyl-N-iso-propylamino-methylsilane |
| N,N-di-sec-butylamino-methylsilane | N-sec-butyl-N-cyclohexylamino- | N-sec-butyl-N-cyclopentylamino- | N-tert-butyl-N-iso-propylamino- |

TABLE 16-continued

Exemplary Organoaminocarbosilane (more specifically organoaminomethylsilane) Compounds

| N-sec-butyl-N-tert-butylamino-methylsilane | N-tert-butyl-N-cyclohexylamino-methylsilane | N-tert-butyl-N-cyclopentylamino-methylsilane | N,N-dicyclohexylamino-methylsilane |
| N-cyclohexyl-N-cyclopentylamino-methylsilane | N-phenyl-N-iso-propylamino-methylsilane | N-sec-butyl-N-phenylamino-methylsilane | N-cyclohexyl-N-phenylamino-methylsilane |
| N-cyclopentyl-N-phenylamino-methylsilane | N-ethyl-N-phenylamino-methylsilane | N,N-dimethylamino-methylsilane | N,N-diethylamino-methylsilane |
| N,N-di-n-propylamino-methylsilane | | | |

TABLE 17

Exemplary Organoaminocarbosilane (more specifically organoaminophenylsilane) Compounds

| N-methyl-N-iso-propylamino-phenylsilane | N-sec-butyl-N-methylamino-phenylsilane | N-cyclohexyl-N-methylamino-phenylsilane | N-methyl-N-cyclopentylamino-phenylsilane |

TABLE 17-continued

Exemplary Organoaminocarbosilane (more specifically organoaminophenylsilane) Compounds

| | | | |
|---|---|---|---|
| N-ethyl-N-iso-propylamino-phenylsilane | N-sec-butyl-N-ethylamino-phenylsilane | N-ethyl-N-cyclohexylamino-phenylsilane | N-ethyl-N-cyclopentylamino-phenylsilane |
| N-n-propyl-N-iso-propylamino-phenylsilane | N-sec-butyl-N-n-propylamino-phenylsilane | N-cyclohexyl-N-n-propylamino-phenylsilane | N-cyclopentyl-N-n-propylamino-phenylsilane |
| N,N-di-iso-propylamino-phenylsilane | N-sec-butyl-N-iso-propylamino-phenylsilane | N-cyclohexyl-N-iso-propylamino-phenylsilane | N-cyclopentyl-N-iso-propylamino-phenylsilane |
| N,N-di-sec-butylamino-phenylsilane | N-sec-butyl-N-cyclohexylamino-phenylsilane | N-sec-butyl-N-cyclopentylamino-phenylsilane | N-tert-butyl-N-iso-propylamino-phenylsilane |
| N-sec-butyl-N-tert-butylamino- | N-tert-butyl-N-cyclohexylamino- | N-tert-butyl-N-cyclopentylamino- | N,N-dicyclohexylamino-phenylsilane |

TABLE 17-continued

Exemplary Organoaminocarbosilane (more specifically organoaminophenylsilane) Compounds N-cyclohexyl-N-cyclopentylamino-phenylsilane N-phenyl-N-iso-propylamino-phenylsilane N-sec-butyl-N-phenylamino-phenylsilane N-cyclohexyl-N-phenylamino-phenylsilane N-cyclopentyl-N-phenylamino-phenylsilane N-ethyl-N-phenylamino-phenylsilane N,N-dimethylamino-phenylsilane N,N-diethylamino-phenylsilane N,N-di-n-propylamino-phenylsilane In another embodiment of the method described herein, the compound selected from orgnoaminosilane, organoaminodisilane, or organoaminocarbosilane is reacted with a proton source to provide an organoamine. In this embodiment, the step, of reacting the compound with a proton source, could be performed prior to or after the purification of the compound. The reagents could be combined neat or, alternatively in the presence of a solvent (e.g., at least one of the proton source or the compound is dissolved in solvent). An excess of proton source can be used to drive the reaction to completion, aid in the purification process, or both. Alternatively, a slight deficiency of the proton source can be used to eliminate the need of separating unreacted proton source from the organoamine product. In one particular embodiment, the proton source is delivered as a vapor into the reaction solution comprising the organoaminosilane. The protonation step (e.g., reaction of the proton source with the compound) could be performed in the temperature range between −50° C. to 150° C. for the addition of reagents and/or for the extent of the reaction. In some embodiments, the protonation step may be carried out at lower temperature (below 0° C.) in order to help remove heat and prevent side reactions. In other embodiments, higher temperatures (above 30° C.) may be preferred to drive the intended protonation reaction to completion. Reaction times could range from 5 minutes to 30 minutes, to 1 h, to 6 h, to 12 h, to 24 hr or more. The protonation reaction mixture may likely yield more than one phase (liquid-liquid or liquid-solid) which can be separated by filtration, decantation, separator funnel, distillation, adsorption, centrifugation, or other means. Purification of the end organoamine product may be accomplished by distillation, column chromatography, gas chromatography, sublimation, crystallization, or other purification processes.

The following examples illustrate the method described herein for preparing compounds such as, without limitation organoaminosilanes, organoaminodisilanes, organoaminocarbosilanes, and is not intended to limit it in any way.

EXAMPLES

For the following examples, gas chromatography (GC-TCD), mass spectrometry (GC-MS), and $^1$H NMR spectroscopy were used to identify and quantify the solution compositions as appropriate. Gas chromatographic analyses were carried out on the product effluent using a TCD equipped HP-5890 Series II GC and a 0.53 mm diameter x 30 m Supleco column containing 3 μm thick SPB-5 media. Chloride analyses were performed by hydrolyzing the sample with water at 85° C. and injecting the liquid phase into a Metrohm Ion Chromatography instrument equipped with a conductivity detector.

Example 1

Synthesis of N,N-di-iso-propylaminosilane (cf. Table 2)

The catalyst $Ru_3(CO)_{12}$ (0.10 g, 0.16 mmol) was dissolved in the imine N-iso-propylidene-iso-propylamine (7.0 g, 71 mmol) and the resulting solution was exposed to a silica source $SiH_4$ gas at 82 psia for 6 hours at 40° C. The resulting reaction solution was determined by GC-MS to contain N,N-di-iso-propylaminosilane. GC-MS showed the following peaks: 131 (M+), 126 (M-15), 116, 110, 98, 88, 74.

Example 2

Synthesis of N,N-di-iso-propylaminodisilane (cf. Table 3)

The catalyst $Ru_3(CO)_{12}$ (0.10 g, 0.16 mmol) was dissolved in the imine N-iso-propylidene-sec-butylamine (7.0 g, 71 mmol) and the resulting solution was exposed to a disilane $Si_2H_6$ gas at 102 psia for 6 hours at 40° C. The reaction solution was determined by GC-MS to contain N,N-di-iso-propylaminodisilane. GC-MS showed the following peaks: 161 (M+), 146 (M-15), 128, 114, 104, 88, 72.

Example 3

Synthesis of 1-(N,N-di-iso-propylamino)-1,4-disilabutane (cf. Table 5)

A mixture of a silica source 1,4-disilabutane (0.48 g, 5.3 mmol) and the imine N-iso-propylidene-iso-propylamine (0.25 g, 2.5 mmol) was added to a stirred suspension of the catalyst, anhydrous $NiCl_2$ (0.02 g, 0.15 mmol) in tetrahyrdofuran (THF) (1 mL), in a nitrogen-filled glovebox. After 2 days of stirring at room temperature, the resulting brown mixture was filtered to remove catalyst sediments and was determined by GC and GC-MS to contain the end product 1-(N,N-di-iso-propylamino)-1,4-disilabutane. GC-MS showed the following peaks: 189 (M+), 188 (M−1), 174 (M-15), 159, 144, 130, 102.

Example 4

Synthesis of 1-(N,N-di-sec-butylamino)-1,4-disilabutane (cf. Table 5)

A mixture of a silica source 1,4-disilabutane (0.50 g, 5.54 mmol) and the imine N-sec-butylidene-sec-butylamine (0.35 g, 2.75 mmol) was added to a stirred solution of the catalyst $(Ph_3P)_3RhCl$ (0.02 g, 0.02 mmol) in THF (0.5 mL). After 1 day of stirring, the imine was completely consumed, and the resulting orange solution was determined by GC and GC-MS to contain the end product 1-(N,N-di-sec-butylamino)-1,4-disilabutane. GC-MS showed the following peaks: 217 (M+), 202 (M-15), 189, 172, 158, 144, 132, 114, 102.

Example 5

Synthesis of 1-(N-sec-butyl-N-iso-propylamino)-1,4-disilabutane (cf. Table 5)

A mixture of a silica source 1,4-disilabutane (0.50 g, 5.54 mmol) and the imine N-sec-butylidene-iso-propylamine (0.32 g, 2.83 mmol) was added to a stirred solution of the catalyst $(Ph_3P)_3RhCl$ (0.02 g, 0.02 mmol) in THF (0.5 mL). After 1 day of stirring, the imine was completely consumed, and the resulting orange solution was determined by GC and GC-MS to contain the end product 1-(N-sec-butyl-N-iso-propylamino)-1,4-disilabutane. GC-MS showed the following peaks: 203 (M+), 188 (M-15), 174, 158, 144, 130, 119, 102.

Example 6

Synthesis of 1-(N,N-di-iso-propylamino)-1-methyl-silacyclopentane (cf. Table 12)

The solid catalyst $Ca[N(SiMe_3)_2]_2$ (0.01 g, 0.03 mmol) was added to a mixture of a silica source 1-methyl-1-silacyclopentane (0.15 g, 1.5 mmol) and the imine N-iso-propylidene-iso-propylamine (0.15 g, 1.5 mmol). After 2 weeks, the pale yellow reaction solution was determined by GC and GC-MS to contain 1-(N,N-di-iso-propylamino)-1-methyl-1-silacyclopentane as the major product. GC-MS showed the following peaks: 199 (M+), 179, 164, 148, 134, 122, 107, 91, 81, 77.

Example 7

Synthesis of N,N-di-iso-propylamino-phenylsilane (cf. Table 17)

A solution of the catalyst $(Ph_3P)_3RhCl$ (0.01 g, 0.01 mmol) in THF (1 mL) was added to a stirred solution of a silica source phenylsilane (0.30 g, 2.77 mmol) and the imine N-iso-propylidene-iso-propylamine (0.12 g, 1.21 mmol). After 1 day of stirring, the imine was almost completely consumed, and the resulting orange solution was determined by GC and GC-MS to contain N,N-di-iso-propylamino-phenylsilane as the major product. GC-MS showed the following corresponding peaks: 207 (M+), 192 (M-15), 177, 164, 150, 134, 121, 107, 86, 72. Minor products observed include N,N-di-iso-propylaminosilane, bis(N,N-di-iso-propylamino)silane, and diphenylsilane.

Comparative Example 8

Synthesis of N,N-di-n-propylaminodiethylsilane using chlorosilane

Traditional method to make organoaminocarbosilane: Chlorodiethysilane (18.5 g, 151 mmol) was added dropwise to a stirred solution of di-n-propylamine (32.1 g, 317 mmol) in hexanes (250 mL) at −15° C. The resulting white slurry was allowed to warm to room temperature while stirring. The white solids were removed by filtration and the colorless filtrate was purified by vacuum distillation to obtain 22.2 g of N,N-di-n-propylaminodiethylsilane. GC-MS showed the following peaks: 187 (M+), 172 (M-15), 158, 144, 130, 116, 100, 87, 72. This product was determined after hydrolysis to contain 537 ppm chloride.

Example 8

Synthesis of N,N-di-n-propylaminodiethylsilane

Claimed method to make organoaminocarbosilane: A solution of the catalyst $(Ph_3P)_3RhCl$ (0.40 mL, 0.029 M, 0.012 mmol) in THF was added to a stirred solution of a silica source diethylsilane (14.6 g, 165 mmol) and the imine N-n-propylidene-n-propylamine (14.4 g, 145 mmol). After 3 days of stirring, the reaction solution was purified by vacuum distillation to obtain 21.4 g of N,N-di-n-propylaminodiethylsilane. This product was determined after hydrolysis to contain 22 ppm chloride, demonstrating the hydrosilylation route provides much less chloride contamination than the route employing chlorosilanes as starting material. Furthermore, the chloride (or other halide) content can be reduced to non-detectable if halide-free catalysts are being employed in the hydrosilylation.

Examples 9-21

Synthesis of Additional Organoaminosilane, Organoaminodisilane, or Organoaminocarbosilane Compounds Additional organoaminosilanes, organoaminodisilanes, and organoaminocarbosilanes were made via similar fashion as Examples 1 to 8 and were characterized by GC-MS. The molecular weight (MW), the structure, and corresponding major MS fragmentation peaks of each compound are provided in Table 18 to confirm their identification.

TABLE 18

Organoaminosilane, organoaminodisilane, or organoaminocarbosilane compounds synthesized via hydrosilylation of imines.

| Ex. | Precursor Name | MW | Structure | MS Peaks |
|---|---|---|---|---|
| 9 | N-sec-butyl-N-iso-propylaminosilane (cf. Table 2) | 145.32 | 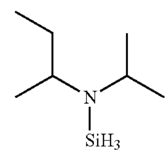 | 145, 130, 116, 100, 88, 74 |
| 10 | N,N-di-sec-butylaminosilane (cf. Table 2) | 159.35 | 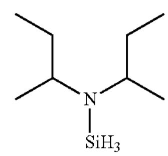 | 159, 144, 130, 114, 100, 88, 74, |
| 11 | N-sec-butyl-N-iso-propylaminodisilane (cf. Table 3) | 175.42 | 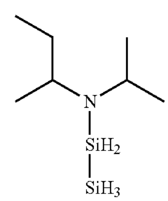 | 175, 160, 146, 128, 114, 104, 86, 72 |
| 12 | N,N-di-sec-butylaminosilane (cf. Table 3) | 189.45 | 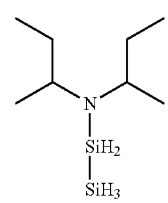 | 189, 174, 160, 142, 128, 118, 104, 86, 72 |
| 13 | 1,2-bis(N,N-di-iso-propylamino)disilane (cf. Table 4) | 260.57 | 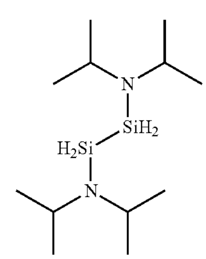 | 260, 245, 229, 215, 187, 173, 158, 144, 128, 116, 100, 86 |

TABLE 18-continued

Organoaminosilane, organoaminodisilane, or organoaminocarbosilane compounds synthesized via hydrosilylation of imines.

| Ex. | Precursor Name | MW | Structure | MS Peaks |
|---|---|---|---|---|
| 14 | 1,2-bis(N-sec-butyl-N-iso-propylamino)disilane (cf. Table 4) | 288.63 | 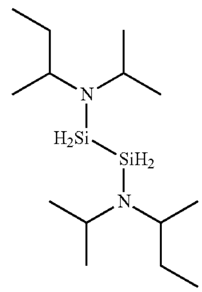 | 288, 273, 259, 172, 158, 144, 130, 116, 100, 86, 72 |
| 15 | 1-(N-n-propyl-N-iso-propylamino)-1,4-disilabutane (cf. Table 5) | 189.45 | 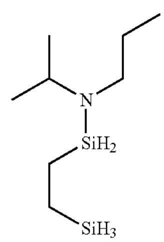 | 189, 174, 160, 144, 130, 116, 102, 86 |
| 16 | 1,4-bis(N-n-propyl-N-iso-propylamino)-1,4-disilabutane (cf. Table 6) | 288.63 | 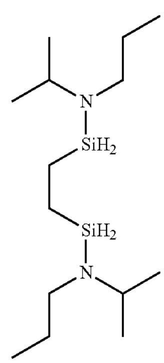 | 288, 274, 260, 244, 230, 216, 201, 188, 173, 160, 144, 128 |
| 17 | 1,4-bis(N,N-di-iso-propylamino)-1,4-disilabutane (cf. Table 6) | 288.63 | 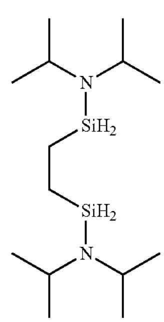 | 288, 287, 243, 229, 207, 188, 144, 130 |

TABLE 18-continued

Organoaminosilane, organoaminodisilane, or organoaminocarbosilane compounds synthesized via hydrosilylation of imines.

| Ex. | Precursor Name | MW | Structure | MS Peaks |
|---|---|---|---|---|
| 18 | 1,4-bis(N-sec-butyl-N-iso-propylamino)-1,4-disilabutane (cf. Table 6) | 316.68 | 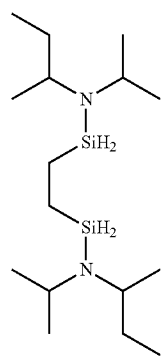 | 316, 301, 281, 257, 243, 229, 215, 202, 186, 172, 158 |
| 19 | 1-(N,N-di-iso-propylamino)-silacyclopentane (cf. Table 11) | 185.39 | 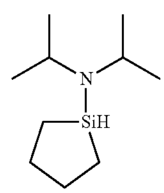 | 185, 170, 154, 142, 128, 112, 99, 85, 70 |
| 20 | 1-(N,N-di-iso-propylamino)-1,3-disilacyclobutane (cf. Table 14) | 187.43 | 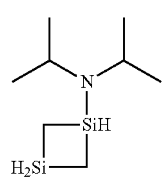 | 187, 172, 159, 143, 130, 115, 101, 86, 73 |
| 21 | 1,3-bis(N,N-di-iso-propylamino)-1,3-disilacyclobutane (cf. Table 15) | 286.61 | 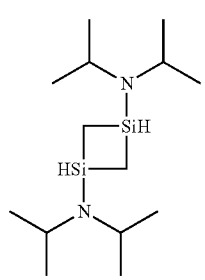 | 286, 271, 243, 229, 213, 186, 172, 144, 128, 101, 87, 70 |

The invention claimed is:

1. An organoaminocarbosilane compound represented by the following structures:

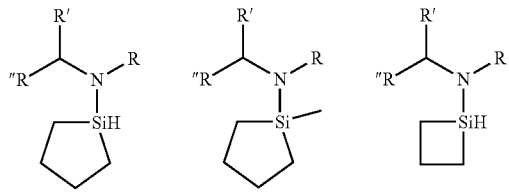

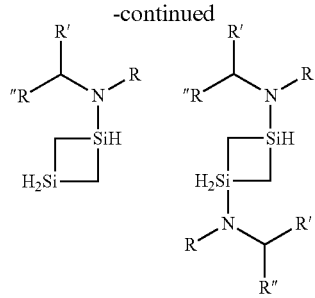

wherein R, R' and R" are each independently selected from hydrogen, a $C_{1-10}$ linear alkyl group, a $C_{3-10}$ branched alkyl group, a $C_{3-10}$ cyclic alkyl group, a $C_{2-10}$ alkenyl group, a $C_{4-10}$ aromatic group, a $C_{4-10}$ heterocyclic group, a $C_{1-10}$ linear organoamino group, a $C_{2-10}$ branched organoamino group, a silyl group, a $C_{1-10}$ linear carbosilyl group, and a $C_{2-10}$ branched carbosilyl group and wherein at least one of R' and R" or R and R' or none of R' and R" or R and R' are linked to form substituted or unsubstituted cyclic ring.

* * * * *